(12) United States Patent
Muraki et al.

(10) Patent No.: US 9,915,935 B2
(45) Date of Patent: Mar. 13, 2018

(54) MICROCHIP-TYPE OPTICAL MEASURING APPARATUS AND OPTICAL POSITION ADJUSTING METHOD THEREOF

(71) Applicant: Sony Corporation, Tokyo (JP)

(72) Inventors: Yosuke Muraki, Tokyo (JP); Fumitaka Otsuka, Tokyo (JP)

(73) Assignee: Sony Corporation, Tokyo (JP)

( * ) Notice: Subject to any disclaimer, the term of this patent is extended or adjusted under 35 U.S.C. 154(b) by 551 days.

(21) Appl. No.: 14/386,499

(22) PCT Filed: Jan. 28, 2013

(86) PCT No.: PCT/JP2013/051800
§ 371 (c)(1),
(2) Date: Sep. 19, 2014

(87) PCT Pub. No.: WO2013/145836
PCT Pub. Date: Oct. 3, 2013

(65) Prior Publication Data
US 2015/0057787 A1 Feb. 26, 2015

(30) Foreign Application Priority Data

Mar. 30, 2012 (JP) ................. 2012-080472

(51) Int. Cl.
G06N 7/00 (2006.01)
G05B 19/27 (2006.01)
G01N 15/14 (2006.01)

(52) U.S. Cl.
CPC ......... *G05B 19/27* (2013.01); *G01N 15/1434* (2013.01); *G01N 15/1484* (2013.01); *G06N 7/005* (2013.01); *G01N 2015/1452* (2013.01)

(58) Field of Classification Search
None
See application file for complete search history.

(56) References Cited

U.S. PATENT DOCUMENTS 5,602,039 A 2/1997 Van Den Engh
5,700,692 A 12/1997 Sweet
(Continued)

FOREIGN PATENT DOCUMENTS

JP 61-029737 A 2/1986
JP 62-036542 A 2/1987
(Continued)

OTHER PUBLICATIONS

U.S. Appl. No. 13/788,075, filed Mar. 7, 2013, Muraki et al.
(Continued)

*Primary Examiner* — Isaac T Tecklu
(74) *Attorney, Agent, or Firm* — Wolf, Greenfield & Sacks, P.C.

(57) ABSTRACT

To provide a microchip-type optical measuring apparatus which is able to automatically perform position adjustment of a microchip with respect to an optical axis of laser with high accuracy.
A microchip-type optical measuring apparatus includes an irradiation detection unit which detects light generated by irradiating a microchip with laser, a position adjustment unit which changes a relative position of the microchip with respect to the irradiation detection unit, and a control unit which outputs a movement signal for a position in which an integrated value or an average value of a detected intensity of the light in a preset region becomes high to the position adjustment unit.

20 Claims, 13 Drawing Sheets

(56) References Cited

U.S. PATENT DOCUMENTS

| | | | |
|---|---|---|---|
| 6,013,168 A * | 1/2000 | Arai | G01N 27/44721 204/601 |
| 6,248,590 B1 | 6/2001 | Malachowski | |
| 6,280,960 B1 * | 8/2001 | Carr | G01N 15/1463 356/244 |
| 6,372,506 B1 | 4/2002 | Norton | |
| 6,538,229 B1 * | 3/2003 | Bogner | B23K 1/0056 219/121.64 |
| 6,941,005 B2 | 9/2005 | Lary et al. | |
| 7,417,734 B2 | 9/2008 | Kanda | |
| 8,681,335 B2 | 3/2014 | Sharpe et al. | |
| 9,029,724 B2 | 5/2015 | Hashimoto et al. | |
| 9,087,371 B2 | 7/2015 | Muraki | |
| 9,339,823 B2 | 5/2016 | Muraki et al. | |
| 9,784,659 B2 | 10/2017 | Tanase et al. | |
| 9,784,660 B2 | 10/2017 | Otsuka et al. | |
| 2002/0141902 A1 | 10/2002 | Ozasa | G01N 15/1434 422/82.09 |
| 2004/0086159 A1 | 5/2004 | Lary et al. | |
| 2007/0195310 A1 | 8/2007 | Kanda | |
| 2008/0255705 A1 | 10/2008 | Degeal et al. | |
| 2009/0027769 A1 * | 1/2009 | Saito | G02B 9/60 359/385 |
| 2009/0111675 A1 * | 4/2009 | Yokogawa | B01L 3/50273 494/37 |
| 2010/0315639 A1 * | 12/2010 | Muraki | G01N 15/1484 356/342 |
| 2011/0069492 A1 * | 3/2011 | van den Engh | G01N 15/14 362/284 |
| 2011/0259749 A1 | 10/2011 | Kanda | |
| 2011/0267604 A1 * | 11/2011 | Swalwell | G01N 15/1434 356/152.1 |
| 2012/0200857 A1 | 8/2012 | Sharpe et al. | |
| 2012/0250018 A1 * | 10/2012 | Tanase | G01N 15/1434 356/338 |
| 2013/0256136 A1 | 10/2013 | Muraki et al. | |
| 2013/0258075 A1 | 10/2013 | Muraki et al. | |
| 2014/0087453 A1 | 3/2014 | Tahara | |
| 2014/0144817 A1 | 5/2014 | Hashimoto et al. | |
| 2014/0193059 A1 | 7/2014 | Muraki | |
| 2014/0208875 A1 | 7/2014 | Muraki | |
| 2014/0212917 A1 * | 7/2014 | Durack | G01N 15/1427 435/34 |
| 2015/0068957 A1 | 3/2015 | Otsuka et al. | |
| 2015/0204774 A1 | 7/2015 | Ito | |
| 2015/0285726 A1 | 10/2015 | Tanase et al. | |
| 2015/0285727 A1 | 10/2015 | Muraki | |
| 2015/0377763 A1 | 12/2015 | Brun et al. | |
| 2016/0223451 A1 | 8/2016 | Muraki et al. | |
| 2016/0245736 A1 | 8/2016 | Muraki et al. | |
| 2016/0266027 A1 | 9/2016 | Muraki et al. | |

FOREIGN PATENT DOCUMENTS

| | | |
|---|---|---|
| JP | 62-100643 A | 5/1987 |
| JP | 64-012245 A | 1/1989 |
| JP | 09-189653 A | 7/1997 |
| JP | 2002-505423 A | 2/2002 |
| JP | 2004-257756 A | 9/2004 |
| JP | 2005-315799 A | 11/2005 |
| JP | 2006-504970 A | 2/2006 |
| JP | 2006-242849 A | 9/2006 |
| JP | 2007-532874 A | 11/2007 |
| JP | 2010-190680 A | 9/2010 |
| JP | 2010-286292 A | 12/2010 |
| JP | 4805417 B1 | 2/2011 |
| JP | 2012-047464 A | 3/2012 |

OTHER PUBLICATIONS

U.S. Appl. No. 13/788,165, filed Mar. 7, 2013, Muraki et al.
U.S. Appl. No. 14/118,788, filed Nov. 19, 2013, Muraki.
U.S. Appl. No. 14/118,994, filed Nov. 20, 2013, Hashimoto et al.
U.S. Appl. No. 14/239,794, filed Feb. 20, 2014, Muraki.
U.S. Appl. No. 14/386,368, filed Sep. 19, 2014, Otsuka et al.
U.S. Appl. No. 14/026,023, filed Sep. 13, 2013, Tahara.
U.S. Appl. No. 14/440,765, filed May 5, 2015, Tanase et al.
U.S. Appl. No. 14/737,370, filed Jun. 11, 2015, Muraki.
U.S. Appl. No. 14/763,980, filed Jul. 28, 2015, Brun et al.
U.S. Appl. No. 14/413,543, filed Jan. 8, 2015, Ito.
U.S. Appl. No. 15/028,411, filed Apr. 8, 2016, Muraki et al.
U.S. Appl. No. 15/028,419, filed Apr. 8, 2016, Muraki et al.
U.S. Appl. No. 15/093,879, filed Apr. 8, 2016, Muraki et al.
U.S. Appl. No. 15/687,948, filed Aug. 28, 2017, Otsuka et al.

* cited by examiner

FIG. 9
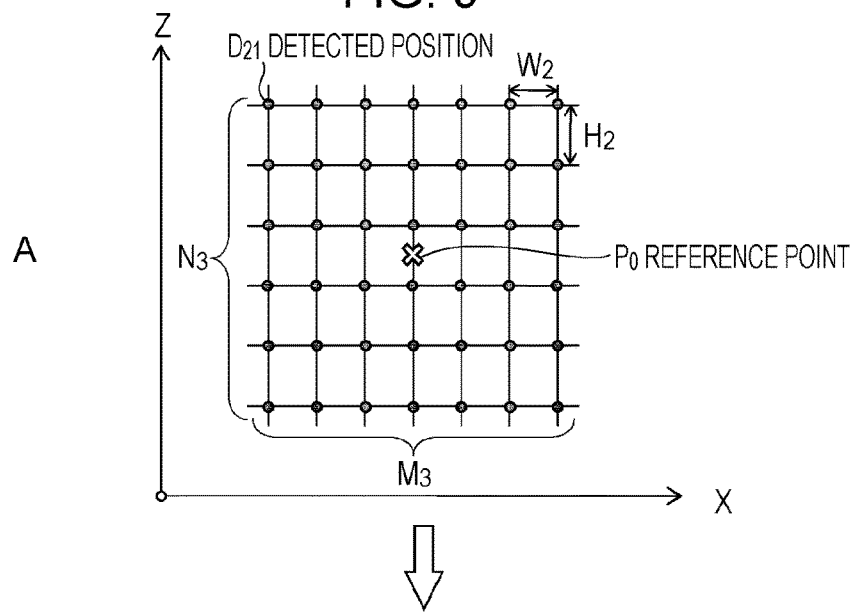
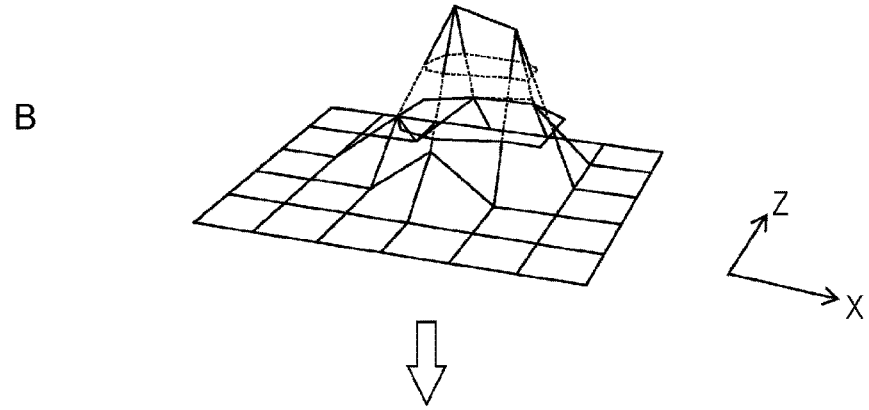
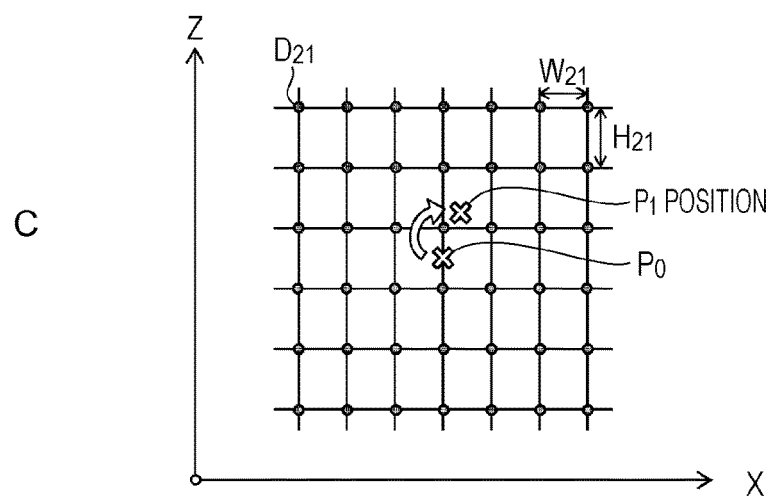

FIG. 10
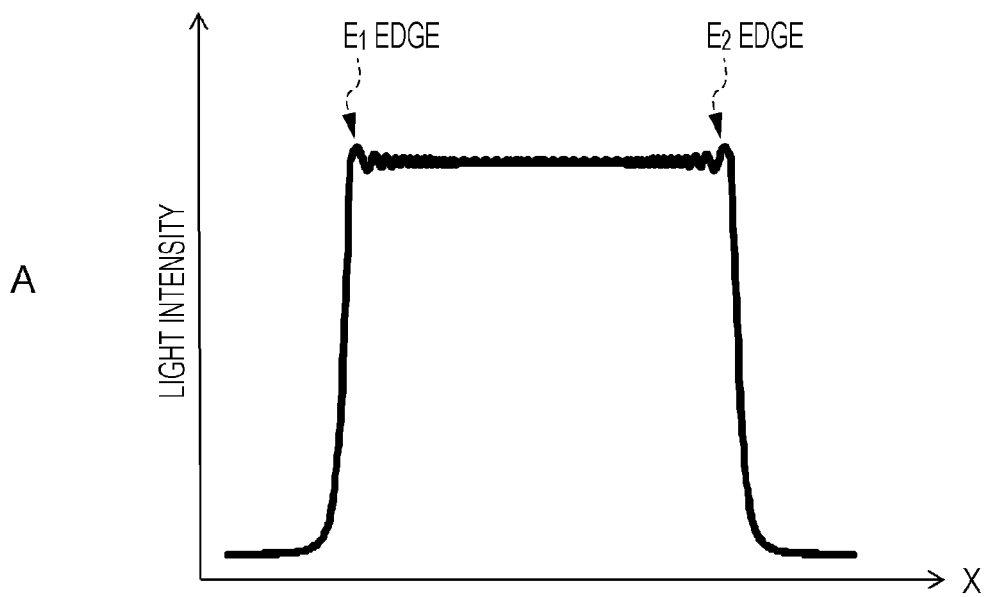
A
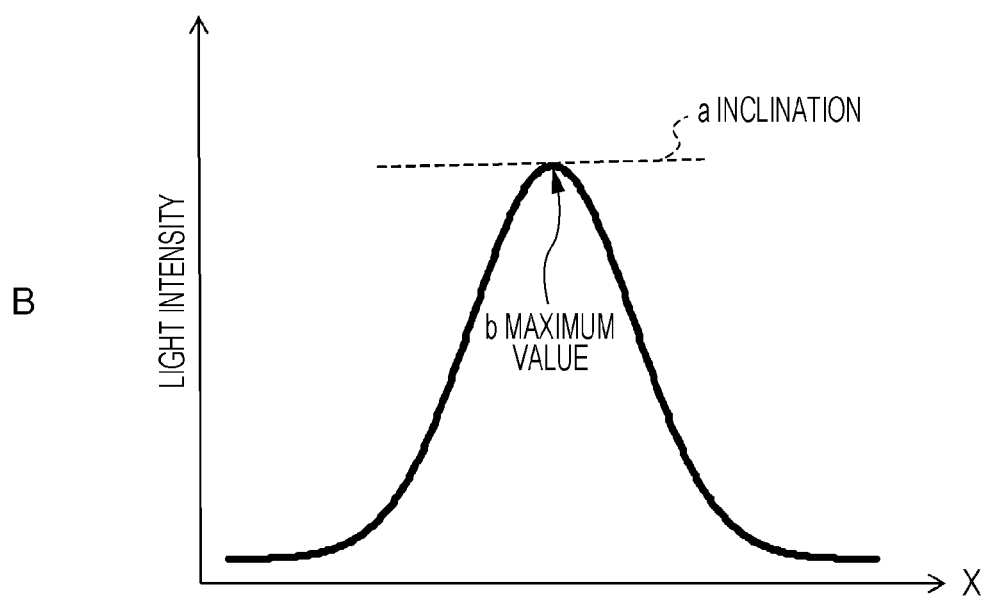
B

FIG. 12
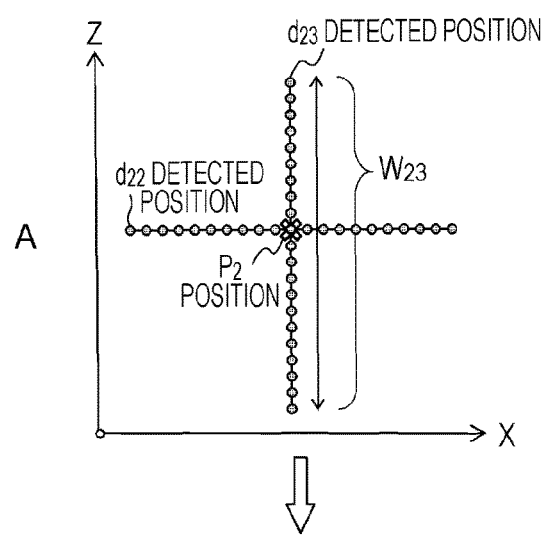
A
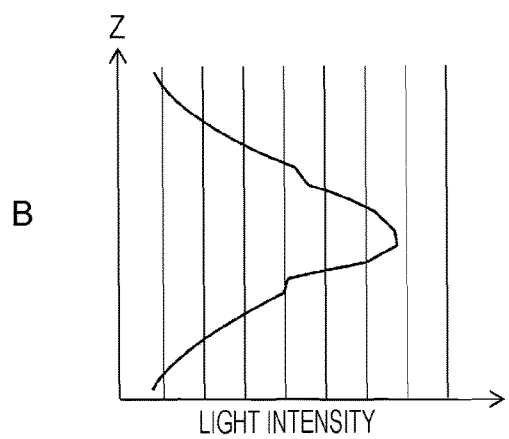
B
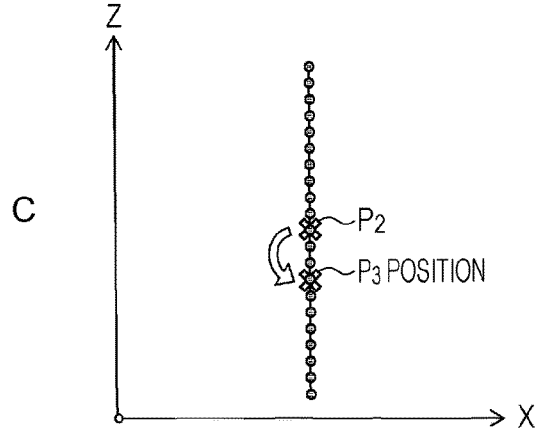
C

MICROCHIP-TYPE OPTICAL MEASURING APPARATUS AND OPTICAL POSITION ADJUSTING METHOD THEREOF

TECHNICAL FIELD

The present technology relates to a microchip-type optical measuring apparatus and an optical position adjusting method thereof. More specifically, the present technology relates to a microchip-type optical measuring apparatus or the like which allows an optical position of a microchip to be automatically optimized and to be measured with high accuracy.

BACKGROUND ART

A microparticle measuring apparatus (for example, a flow cytometer) which optically measures characteristics of a microparticle such as a cell is known.

In the flow cytometer, sample liquid including the cell flows through a flow passage formed in a flow cell or a microchip, and a detector detects fluorescence or scattering light generated from the cell by irradiating the cell which through-flows inside the flow passage with laser, so that an optical characteristic of the cell is measured. In addition, in the flow cytometer, as a measurement result of the optical characteristic, a population (a group) which is determined to satisfy a predetermined condition is separately collected from the cell.

For example, in PTL 1, as a microchip-type flow cytometer, "a microparticle splitting device including a microchip provided with a flow passage through which liquid including a microparticle flows, and an orifice which ejects the liquid flowing through the flow passage into a space outside the chip, an oscillating element for discharging the liquid to be liquid droplets in the orifice, a charging unit for applying an electric charge to the discharged liquid droplets, an optical detection unit which detects optical characteristic of the microparticle flowing through the flow passage, counter electrodes which are disposed to face each other and to interpose the liquid droplets moved along a movement direction of the liquid droplets which are discharged into the space outside the chip, and two or more containers which collect the liquid droplets passed between the counter electrodes" is disclosed.

CITATION LIST

Patent Literature

PTL 1: Japanese Unexamined Patent Application Publication No. 2010-190680

SUMMARY OF INVENTION

Technical Problem

The microparticle measuring apparatus is required to perform position adjustment of a through-flow position of the microparticle inside the flow passage formed in the flow cell or the microchip and an optical axis of the laser with high accuracy, in order to accurately measure the optical characteristic of the microparticle. In the related art, since the position adjustment is manually performed by a user with particles for calibration (calibration beads), the position adjustment requires proficiency, and thus has a problem in reliability or stability. Particularly, in the microchip-type microparticle measuring apparatus, the optical position adjustment is required whenever the microchip is exchanged or is analyzed, and thus the position adjustment is considerably cumbersome and complicated.

Therefore, an object of the present invention is to provide a microchip-type optical measuring apparatus which is able to automatically perform position adjustment of a microchip with respect to an optical axis of laser with high accuracy.

Solution to Problem

In order to solve the problem described above, the present invention provides a microchip-type optical measuring apparatus including an irradiation detection unit which detects light generated by irradiating a microchip with laser, a position adjustment unit which changes a relative position of the microchip with respect to the irradiation detection unit, and a control unit which outputs a movement signal for a position in which an integrated value or an average value of a detected intensity of the light in a preset region becomes high to the position adjustment unit.

In this microchip-type optical measuring apparatus, the control unit may assume that a relationship between a detected position and the integrated value or the average value of the detected intensity of the light follows pre-stored probability distribution, may estimate a distribution parameter of the probability distribution on the basis of a stochastic method, and thus may create the movement signal for the position in which the integrated value or the average value of the detected intensity of the light becomes maximum according to the estimation. The control unit may select the probability distribution according to an irradiation profile of the laser.

In addition, the control unit may output the movement signal for a position in which a variation coefficient of the integrated value or the average value of the detected intensity of the light in a plurality of preset points becomes minimum to the position adjustment unit.

In addition, the control unit may output the movement signal for an area in which an area average of the integrated value of the detected intensity in a plurality of preset areas becomes maximum to the position adjustment unit.

In addition, the control unit may output the movement signal for a position in which the integrated value of the detected intensity in the plurality of preset points becomes maximum to the position adjustment unit.

In addition, the control unit may output the movement signal for a first optimal position in which the integrated value of the detected intensity in the area of a maximum area average becomes maximum, or for a second optimal position in which the variation coefficient in the area of the maximum area average becomes minimum to the position adjustment unit.

In addition, the control unit may output the movement signal for the second optimal position to the position adjustment unit when the first optimal position and the second optimal position are different from each other.

This microchip-type optical measuring apparatus may be configured as a microchip-type microparticle measuring apparatus.

In addition, the present invention provides an optical position adjusting method including a procedure for detecting light which is generated from a microchip by laser irradiation, from a plurality of positions on the microchip, and a procedure for specifying a position in which an integrated value or an average value of a detected intensity of the light in a preset region becomes maximum.

In the procedure for specifying the position, a relationship between a detected position and the integrated value or the average value of the detected intensity of the light may be assumed to follow a pre-stored probability distribution, a distribution parameter of the probability distribution may be estimated on the basis of a stochastic method, and thus the position in which the integrated value or the average value of the detected intensity of the light becomes maximum may be specified by the estimation.

In addition, this optical position adjusting method may further include a procedure for assuming that the integrated value or the average value of the detected intensity of the light from the position in which the integrated value or the average value of the detected intensity of the light is estimated to be maximum by the probability distribution to a predetermined position is in a one-dimensional distribution, and thus for specifying a position in which the integrated value or the average value of the detected intensity of the light becomes maximum by the one-dimensional distribution.

In addition, in the procedure for specifying the position, the position may be set to a position in which a variation coefficient of the integrated value or the average value of the detected intensity of the light in a plurality of preset points becomes minimum.

In addition, this optical position adjusting method may further include a procedure for specifying a position in which an area average of the integrated value of the detected intensity of the light in a plurality of preset areas becomes maximum.

In addition, this optical position adjusting method may further include a procedure for specifying a first optimal position in which the integrated value of the detected intensity in the area of a maximum area average becomes maximum.

In addition, the procedure for specifying the position in which the variation coefficient becomes minimum may be a procedure for specifying a second optimal position in which the variation coefficient in the area of the maximum area average becomes minimum.

In addition, this optical position adjusting method may include a procedure for setting a relative position of the microchip with respect to the laser to the first optimal position or the second optimal position.

Further, the present invention provides an optical position adjusting method of a microchip-type optical measuring apparatus, including a procedure for detecting light which is generated from a microchip by laser irradiation, from a plurality of positions on the microchip, a procedure for specifying a position in which an area average of an integrated value of a detected intensity of the light becomes high, a procedure for specifying a first optimal position in which the integrated value or an average value of the detected intensity in an area where the area average becomes higher, becomes higher, a procedure for specifying a second optimal position in which a variation coefficient of the integrated value or the average value of the detected intensity in the area where the area average becomes higher, becomes smaller, and a procedure for setting a relative position of the microchip with respect to the laser to the first optimal position or the second optimal position.

In the present technology, a cell or a microbe, a biologically-relevant microparticle such as a liposome, or a latex particle or a gel particle, a synthetic particle such as an industrial particle, and the like are broadly included in the "microparticle".

In the biologically-relevant microparticle, a chromosome, a liposome, a mitochondria, an organelle (a cell organelle), and the like which configure various cells are included. In the cell, an animal cell (a blood cell or the like) and a plant cell are included. In the microbe, a bacteria such as a bacteria coliform, a virus such as a tobacco mosaic virus, a fungus such as a Yeast fungus, and the like are included. Further, in the biologically-relevant microparticle, a biologically-relevant polymer such as a nucleic acid or a protein, or a complex thereof is also able to be included. In addition, the industrial particle may be, for example, an organic or inorganic polymeric material, a metal, and the like. In the organic polymeric material, polystyrene, styrene•divinylbenzene, polymethylmethacrylate, and the like are included. In the inorganic polymeric material, glass, silica, a magnetic body material, and the like are included. In the metal, a gold colloid, aluminum, and the like are included. Generally, it is ordinary that the shape of the microparticle is spherical, but the shape may also be non-spherical, and the size, mass, or the like is not particularly limited.

Advantageous Effects of Invention

According to the present invention, a microchip-type optical measuring apparatus which is able to automatically perform position adjustment of a microchip with respect to an optical axis of laser with high accuracy is provided.

BRIEF DESCRIPTION OF DRAWINGS

FIG. 9 is a diagram for describing control of a coarse adjustment step $S_{21}$ according to the second embodiment.

FIG. 10 is a diagram for describing a fixed distribution assumed in the coarse adjustment step $S_{21}$ according to the second embodiment.

FIG. 12 is a diagram for describing control of a second fine adjustment step $S_{23}$ according to the second embodiment.

DESCRIPTION OF EMBODIMENTS

Hereinafter, best modes for carrying out the present invention will be described with reference to the drawings. Furthermore, embodiments described below indicate an example of a representative embodiment of the present invention, and it is not construed as narrowing the range of the present invention by the embodiments. The description will be provided according to the following order.

Figure 1:
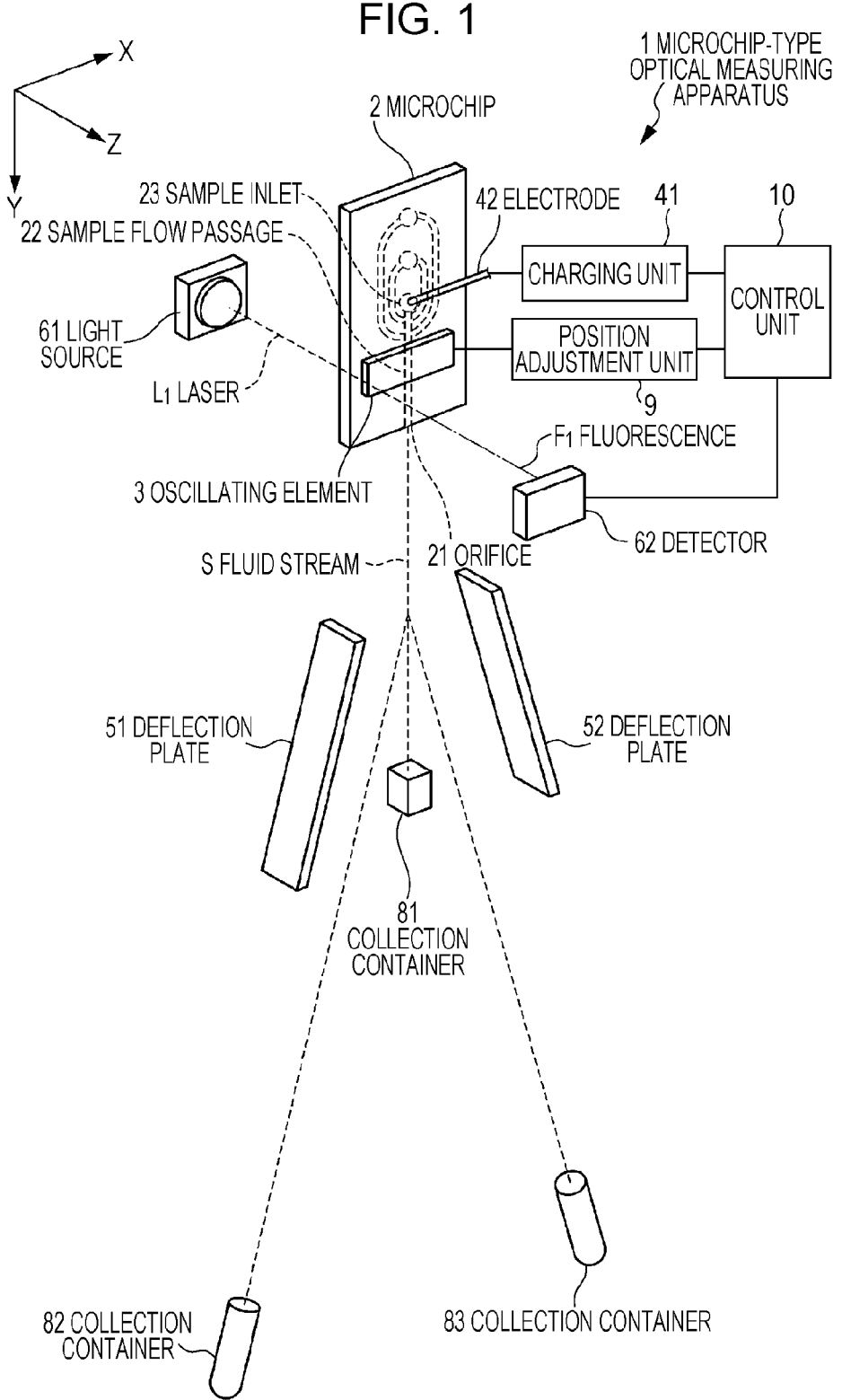
FIG. 1 is a diagram for describing a configuration of a microchip-type optical measuring apparatus 1 (a flow cytometer 1) according to the present invention which is configured as a microchip-type flow cytometer.
Figure 2:
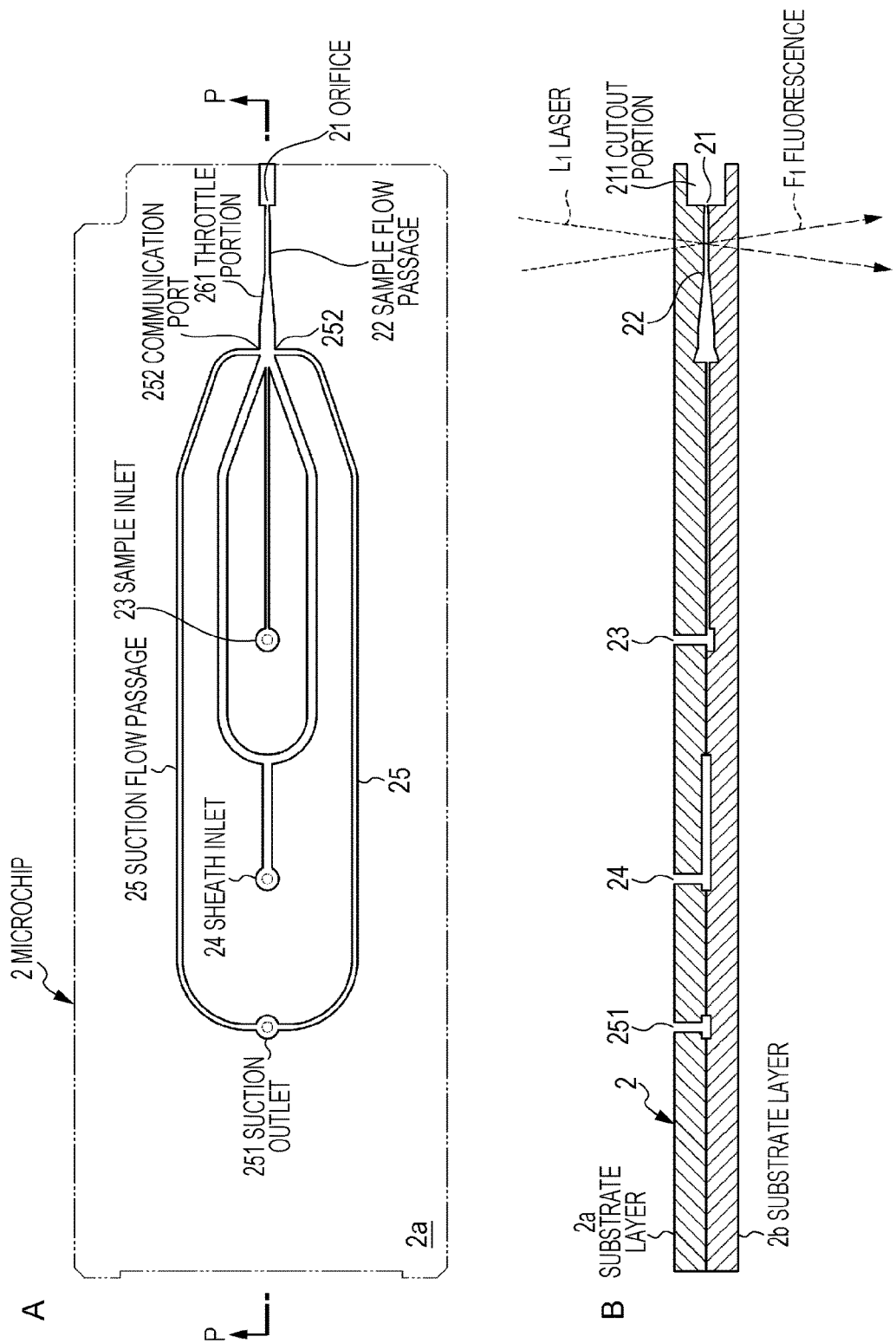
FIG. 2 is a diagram for describing a configuration of an example of a microchip 2 which is mountable on the flow cytometer 1.
Figure 3:
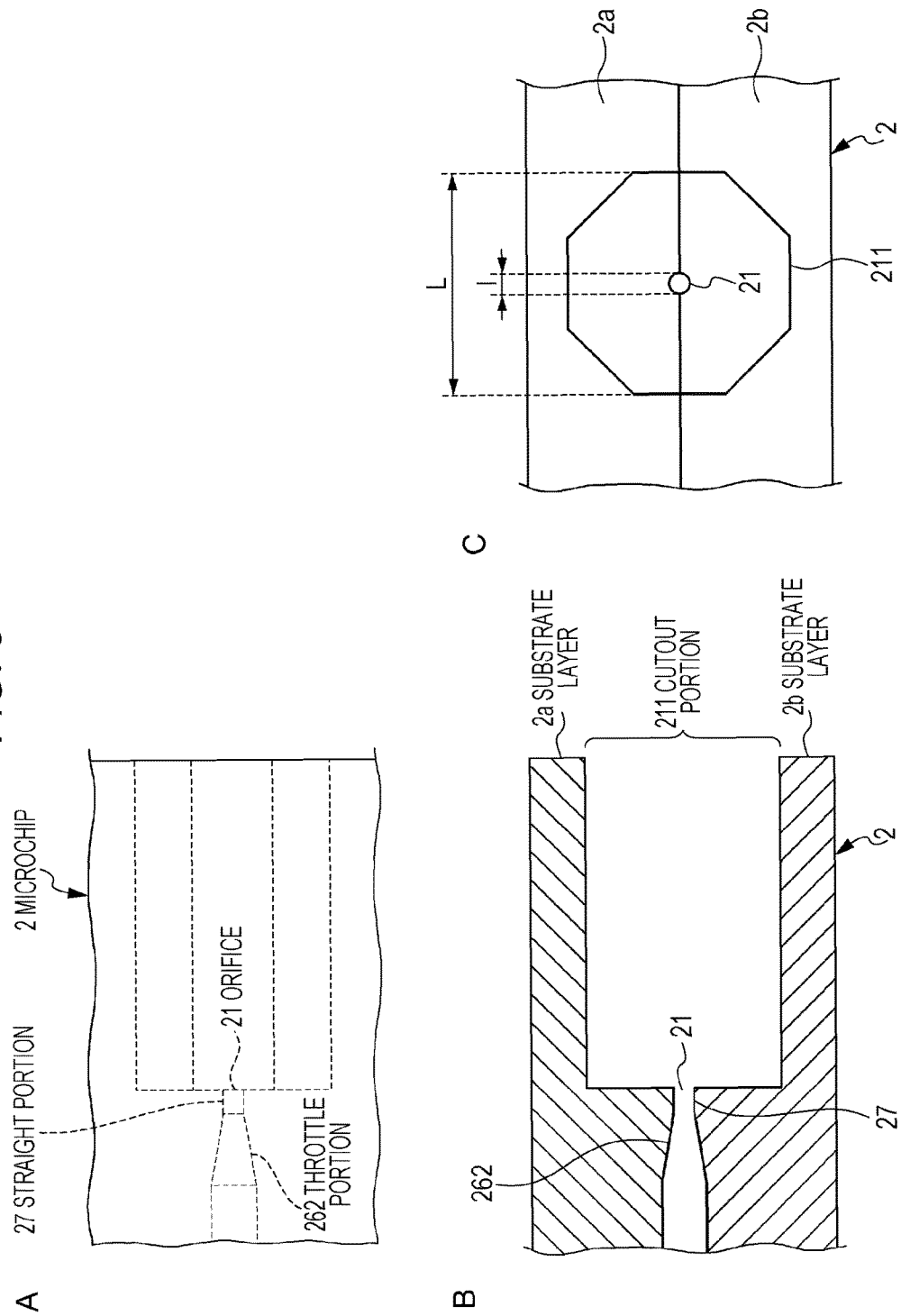
FIG. 3 is a diagram for describing a configuration of an orifice 21 of the microchip 2.

1. Microchip-type Optical Measuring Apparatus
   (1) Irradiation Detection Unit
   (2) Position Adjustment Unit
   (3) Oscillating Element
   (4) Charging Unit
   (5) Deflection Plate
   (6) Collection Container
   (7) Control Unit or the like
   (8) Microchip
2. Optimization Control of Optical Position of Microchip-type Optical Measuring Apparatus according to First Embodiment of the Present Invention
   (1) Original Point•Reference Point Movement Step $S_1$
   (2) Signal Acquisition Step $S_2$
   (3) Area Average Value Maximum Position Determination Step $S_3$
   (4) Area Average Maximum Position Movement Step $S_4$
   (5) Signal Acquisition Step $S_5$
   (6) Integrated Value Maximum Position Determination Step $S_6$
   (7) Variation Coefficient Determination Step $S_7$
   (8) Position Optimization Step $S_8$
3. Optimization Control of Optical Position of Microchip-type Optical Measuring Apparatus according to Second Embodiment of the Present Invention
   (1) Coarse Adjustment Step $S_{21}$
   (1-1) Grid-like Signal Acquisition Step $S_{211}$
   (1-2) Two-dimensional Distribution Parameter Estimation Step $S_{212}$
   (1-3) Maximum Position Movement Step $S_{213}$
   (2) First Fine Adjustment Step $S_{22}$
   (2-1) Linear Signal Acquisition Step $S_{221}$
   (2-2) One-dimensional Distribution Parameter Estimation Step $S_{222}$
   (2-3) Maximum Position Movement Step $S_{223}$
   (3) Second Fine Adjustment Step $S_{23}$
   (3-1) Linear Signal Acquisition Step $S_{231}$
   (3-2) One-dimensional Distribution Parameter Estimation Step $S_{232}$
   (3-3) Maximum Position Movement Step $S_{233}$
   (4) Finer Adjustment Step $S_{24}$ 1. Microchip-Type Optical Measuring Apparatus FIG. 1 is a schematic diagram for describing a configuration of a microchip-type optical measuring apparatus 1 (hereinafter, referred to as a "flow cytometer 1") according to the present technology which is configured as a microchip-type flow cytometer. In addition, FIG. 2 and FIG. 3 illustrate an example of a microchip 2 which is mountable on the flow cytometer 1. FIG. 2A illustrates a schematic upper surface view, and FIG. 2B illustrates a schematic sectional view corresponding to a cross-section cut along line P-P of FIG. 2A. In addition, FIG. 3 is a diagram for schematically describing a configuration of an orifice 21 of the microchip 2, and FIG. 3A illustrates an upper surface view, FIG. 3B illustrates a sectional view, and FIG. 3C illustrates a front view. FIG. 3B corresponds to the cross-section cut along line P-P of FIG. 2A.

(1) Irradiation Detection Unit

The flow cytometer 1 is provided with an irradiation detection unit which includes a light source 61 for irradiating the microchip 2 with laser $L_1$, and a detector 62 for detecting light to be detected which is generated by irradiation of the laser $L_1$. An irradiation direction of the laser $L_1$ with respect to the microchip 2 (an optical axis of the laser $L_1$) is illustrated as a Z-axis forward direction of FIG. 1. The light source 61 may be an LD, an LED, or the like.

The laser $L_1$ is applied into a cell which flows through a sample flow passage 22 of the microchip 2. The detector 62 detects scattering light of the laser $L_1$ caused by the cell, and fluorescence generated by exciting the cell or fluorescent pigment marked on the cell with the laser $L_1$. In FIG. 1, the fluorescence generated from the cell which flows through the sample flow passage 22 is indicated by a reference mark $F_1$.

The irradiation detection unit includes an irradiation system provided with a condensing lens for condensing light by guiding the laser $L_1$ emitted from the light source 61 to the cell, a dichroic mirror, a band pass filter, or the like. In addition, the irradiation detection unit is configured by a detection system for guiding the light to be detected which is generated from the cell by the irradiation of the laser $L_1$ to the detector 62 by condensing the light. The detection system is configured by, for example, a photo multiplier tube (PMT), an area imaging element such as a CCD or a CMOS element, or the like.

The light to be detected which is detected by the detection system of the irradiation detection unit is the light which is generated from the cell by the irradiation of the laser $L_1$, and may be, for example, forward scattering light or lateral scattering light, scattering light such as Rayleigh scattering or Mie scattering, fluorescence, or the like. The fluorescence may be generated from the cell or the fluorescent pigment marked on the cell. The light to be detected is converted to an electric signal, and is used for optical characteristic determination of the cell and automatic adjustment of an optical position (described later).

(2) Position Adjustment Unit

The flow cytometer 1 includes a position adjustment unit 9 which changes a relative position of the microchip 2 with respect to the irradiation detection unit. The position adjustment unit 9 moves the position of the microchip 2 and/or the position of the irradiation detection unit on a plane (an XY plane) perpendicular to the optical axis of the laser $L_1$. Accordingly, the position adjustment unit 9 adjusts the position of the microchip 2 with respect to the optical axis of the laser $L_1$, and optimizes the laser $L_1$ to be applied to a through-flow position of the cell inside the sample flow passage 22.

The position adjustment unit 9 may move at least one of the position of the microchip 2 and the position of the irradiation detection unit including the light source 61 and the detector 62 to an X-axial direction and a Y-axial direction. The position adjustment unit 9 is configured by, for example, a stepping motor or the like. Furthermore, the position adjustment unit 9 may move the relative position of the microchip 2 with respect to the irradiation detection unit to a Z-axial direction (a focus direction of the laser $L_1$).

(3) Oscillating Element

The flow cytometer 1 includes an oscillating element 3 for discharging laminar flow of sample liquid and sheath liquid including the cell which is ejected from the orifice 21 to be liquid droplets by applying oscillation to the orifice 21 formed in the microchip 2. The oscillating element 3 may be, for example, a piezo element. The discharged liquid droplets are injected to a Y-axis forward direction indicated by an arrow in the drawings as fluid stream S. Furthermore, in the flow cytometer 1, the microchip 2 is exchangeably mounted.

In the flow cytometer 1, the oscillating element 3 may be integrated with the microchip 2, and may be disposed on the apparatus side to be contactable with the mounted microchip 2.

(4) Charging Unit

Positive or negative electric charges are applied to the liquid droplets discharged from the orifice 21 by a charging unit 41. The charging of the liquid droplets is performed by an electrode 42 which is electrically connected to the charging unit 41 and inserted into a sample inlet 23 disposed in the microchip 2. Furthermore, the electrode 42 may be inserted into any one portion of the microchip 2 to electrically come in contact with the sample liquid or the sheath liquid flowing through the flow passage.

In the flow cytometer 1, a frequency of a driving voltage of the oscillating element 3, and switching timing of a voltage (a charge voltage) of the charging unit 41 are synchronized, so that any one of plus and minus electric charges is applied to a part of the liquid droplets discharged from the orifice 21. The electric charge may not be applied to a part of the liquid droplets, and thus a part of the liquid droplets may be uncharged.

(5) Deflection Plate

Further, the flow cytometer 1 includes a pair of deflection plates 51 and 52 which are disposed to face each other and to interpose the fluid stream S. The deflection plates 51 and 52 change a travelling direction of each of the liquid droplets in the fluid stream S by an electric force which acts with respect to the electric charges applied to the liquid droplets. The deflection plates 51 and 52 may be an ordinary electrode. In FIG. 1, a facing direction of the polarizing plates 51 and 52 is illustrated by the X-axial direction.

(6) Collection Container

The fluid stream passed between the deflection plates 51 and 52 is received in any one of a collection container 81, a collection container 82, or a collection container 83. For example, when the deflection plate 51 is positively charged and the deflection plate 52 is negatively charged, the liquid droplets which are negatively charged by the charging unit 41 are collected in the collection container 82, and the positively charged liquid droplets are collected in the collection container 83, respectively. In addition, the liquid droplets which are not charged by the charging unit 41 directly drop to be collected in the collection container 81 without receiving an electrical acting force from the deflection plates 51 and 52. In the flow cytometer 1, the travelling direction of the liquid droplets is controlled according to the characteristic of the cell included in each of the liquid droplets, thereby allowing a target cell having a desired characteristic and a non-target cell other than the target cell to be collected in separate collection containers.

The collection containers 81, 82, and 83 may be a general-purpose plastic tube or a glass tube for laboratory use. It is preferable that the collection containers be exchangeably disposed in the flow cytometer 1. In addition, the collection container for receiving the non-target cell among the collection containers may be connected to a drainage route of the collected liquid droplets. Furthermore, in the flow cytometer 1, the number of collection containers to be disposed is not particularly limited. When more than 3 collection containers are disposed, the respective liquid droplets are induced toward any one of the collection containers according to presence or absence of the electrical acting force between the deflection plates 51 and 52, and the magnitude thereof, and collected in the collection container.

(7) Control Unit or the Like

The flow cytometer 1 includes a data analysis unit for determining the optical characteristic of the cell, a tank unit for accumulating the sample liquid and the sheath liquid, a control unit 10 for controlling each configuration, and the like, which are provided in a usual flow cytometer, in addition to the configuration described above.

The control unit 10 is able to be configured by a general-purpose computer provided with a CPU, a memory, hard disk, and the like, and stores an OS, a program for executing a control step (described later), and the like in the hard disk.

The control unit 10 outputs a movement signal for a position in which a variation becomes small, that is, a position in which an integrated value or an average value of a detected intensity of the light generated from the microchip by the irradiation of the laser $L_1$ becomes higher (preferably, becomes a maximum value) among regions set in advance to the position adjustment unit 9.

(8) Microchip

The microchip 2 is configured by bonding substrate layers 2a and 2b in which the sample flow passage 22 is formed. The sample flow passage 22 is able to be formed in the substrate layers 2a and 2b according to injection molding of a thermoplastic resin with a mold. As the thermoplastic resin, plastics which are known as microchip material in the related art, such as polycarbonate, polymethylmethacrylate (PMMA) resin, cyclic polyolefin, polyethylene, polystyrene, polypropylene, and polydimethylsiloxane (PDMS) are able to be adopted.

The sample liquid is introduced to the sample inlet 23, merged into the sheath liquid introduced to a sheath inlet 24, and flows through the sample flow passage 22. The flow of the sheath liquid introduced from the sheath inlet 24 is divided into two directions, and then is merged into the sample liquid at a merging portion with the sample liquid introduced from the sample inlet 23, by sandwiching the sample liquid from the two directions. Accordingly, three-dimensional laminar flow in which sample liquid laminar flow is positioned in the center of sheath liquid laminar flow is formed at the merging portion.

A reference numeral "25" indicates a suction flow passage for removing clogging or air bubbles by applying a negative pressure to the inside of the sample flow passage 22 and by temporarily regurgitating the flow when the clogging or the air bubbles is generated in the sample flow passage 22. One end of the suction flow passage 25 is provided with a suction outlet 251 which is connected to a negative pressure source such as a vacuum pump, and the other end is connected to the sample flow passage 22 at a communication port 252.

A laminar flow width of the three-dimensional laminar flow is narrowed at a throttle portions 261 (refer to FIG. 2) and 262 (refer to FIG. 3) which are formed such that the area of a cross section vertical to a flow direction gradually or progressively becomes smaller upstream to downstream in the flow direction. Subsequently, the three-dimensional laminar flow is ejected from the orifice 21 disposed on one end of the flow passage.

The characteristic of the cell is detected between the throttle portion 261 and the throttle portion 262 of the sample flow passage 22. The cell which is arranged in line at the center of the three-dimensional laminar flow and flows through the sample flow passage 22 is irradiated with the laser $L_1$ by the irradiation detection unit, and thus the fluorescence $F_1$ and the scattering light which are generated from the cell are detected (refer to FIG. 2).

A connection portion with respect to the orifice 21 of the sample flow passage 22 is configured as a straight portion 27 which is linearly formed. The straight portion 27 functions to directly inject the fluid stream S from the orifice 21 to the Y-axis forward direction.

The three-dimensional laminar flow ejected from the orifice 21 becomes the liquid droplets by the oscillation applied to the orifice 21 according to the oscillating element 31, and is injected as the fluid stream S (refer to FIG. 1). The orifice 21 is open to an end surface direction of the substrate layers 2a and 2b, and a cutout portion 211 is formed between an opening position of the orifice and the end surfaces of the substrate layers. The cutout portion 211 is formed by cutting out the substrate layers 2a and 2b between the opening position of the orifice 21 and the end surfaces of the substrates such that the diameter L of the cutout portion 221 is larger than the opening diameter l of the orifice 21 (refer to FIG. 3C). It is preferable that the diameter L of the cutout portion 211 be equal to or greater than two times larger than the opening diameter l of the orifice 21 in order not to disturb the movement of the liquid droplets discharged from the orifice 21.

Figure 4:
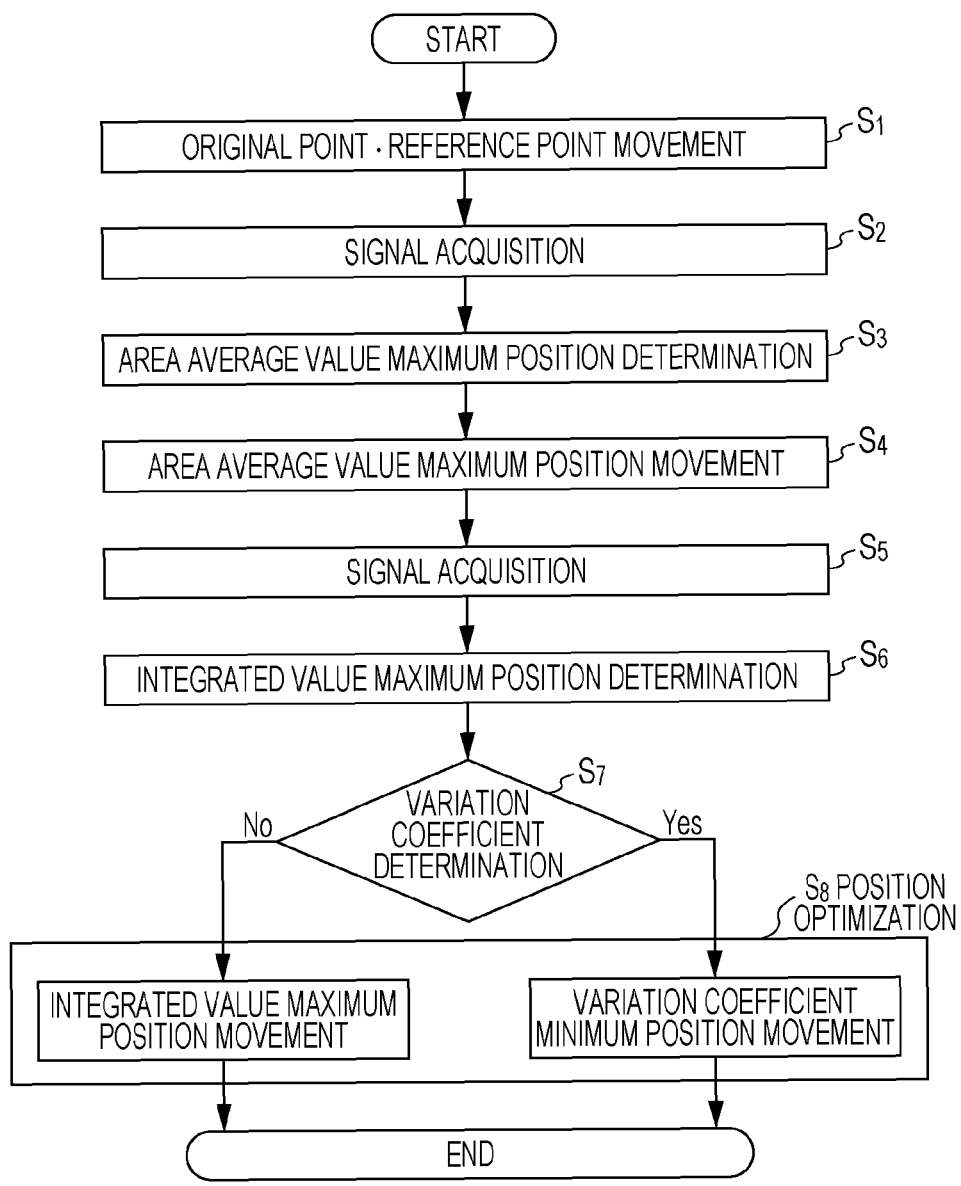
FIG. 4 is a flowchart for describing a control step according to a first embodiment in order to optimize an optical position of the flow cytometer 1.

2. Optimization Control of Optical Position of Microchip-Type Optical Measuring Apparatus According to First Embodiment of the Present Technology FIG. 4 is a flowchart for describing a control step in order to optimize an optical position of the microchip 2 of the flow cytometer 1. The control step includes a procedure of an "original point•reference point movement step $S_1$", a "signal acquisition step $S_2$", an "area average value maximum position determination step $S_3$", an "area average maximum position movement step $S_4$", a "signal acquisition step $S_5$", an "integrated value maximum position determination step $S_6$", a "variation coefficient determination step $S_7$", and a "position optimization step $S_8$". Hereinafter, each procedure will be described.

(1) Original Point•Reference Point Movement Step $S_1$

When a starting signal of an analysis is input by a user, the control unit 10 outputs the movement signal to the position adjustment unit 9, and the position adjustment unit 9 moves the relative position of the microchip 2 with respect to the irradiation detection unit to an initial position (refer to an original point O of FIG. 5) set in advance. When the relative position is at the original point O, the laser $L_1$ emitted from the irradiation detection unit is applied to the original point O on the microchip 2. The relative position is changed by moving at least one of the position of the microchip 2 or the position of the irradiation detection unit including the light source 61 and the detector 62 to the X-axial direction and the Y-axial direction, and, hereinafter, a case where the relative position is changed by moving the position of the microchip 2 will be described as an example.

Next, the control unit 10 starts to allow the sample liquid and the sheath liquid to flow toward the sample inlet 23 and the sheath inlet 24 of the microchip 2 by driving a pump of the tank portion which accumulates the sample liquid and the sheath liquid. It is preferable that the sample liquid include a calibration bead. Further, the control unit 10 starts to apply the oscillation to the orifice 21 by the oscillating element 3. Accordingly, the three-dimensional laminar flow of the sample liquid and the sheath liquid injected from the orifice 21 is discharged to be the liquid droplets, and thus the fluid stream S is generated.

Figure 5:
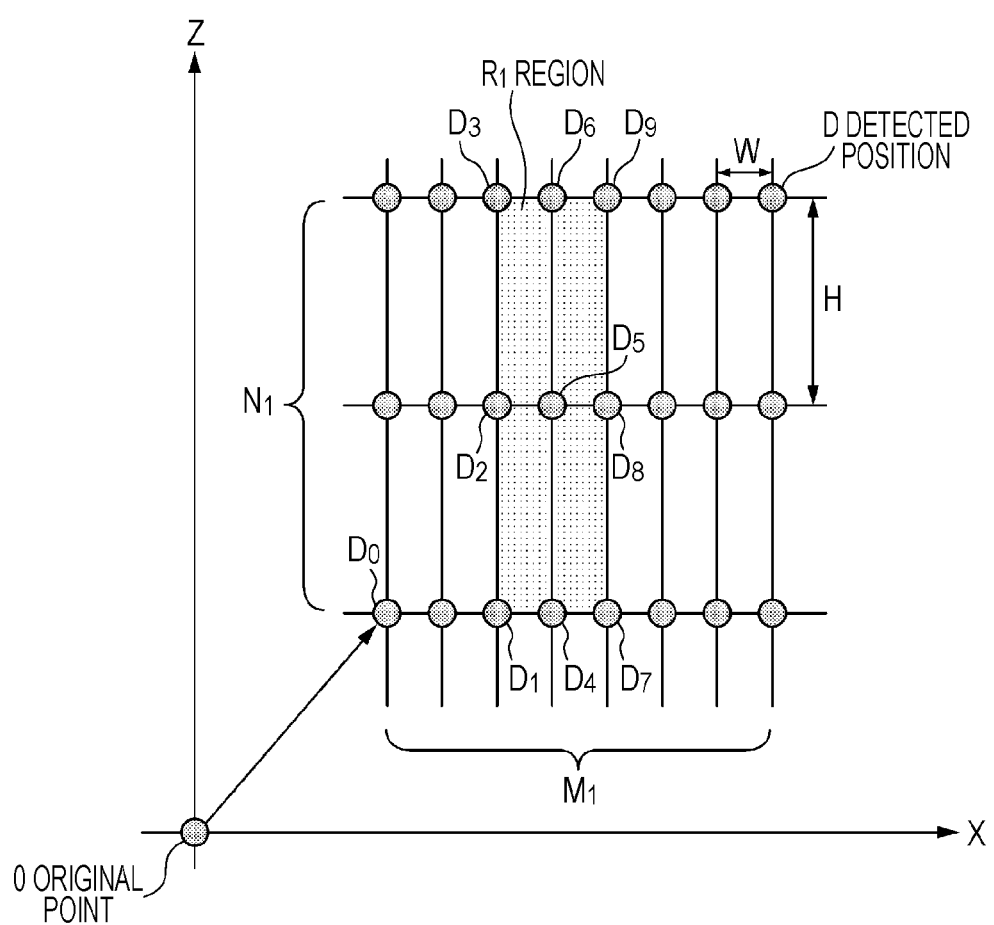
FIG. 5 is a diagram for describing control of an original point•reference point movement step $S_1$ to an area average value maximum position determination step $S_3$ according to the first embodiment.

After starting the flow of the sample liquid and the sheath liquid, the control unit 10 outputs the movement signal to the position adjustment unit 9, and the position adjustment unit 9 moves the position of the microchip 2 to a reference point $D_0$ from the original point O (refer to an arrow of FIG. 5). When the relative position of the microchip 2 with respect to the irradiation detection unit is at the reference point $D_0$, the laser $L_1$ emitted from the irradiation detection unit is applied to the reference point $D_0$ on the microchip 2.

The reference point $D_0$ is set in advance in the vicinity of the position in which the characteristic of the cell of the microchip 2 is able to be detected (that is, an optimal position which is determined by steps described later). More specifically, the reference point $D_0$ is the vicinity between the throttle portion 261 and the throttle portion 262 of the sample flow passage 22 (refer to FIG. 3).

(2) Signal Acquisition Step $S_2$

In this step $S_2$, the fluorescence or the scattering light (hereinafter, simply referred to as the "fluorescence") generated from a plurality of positions on the microchip 2 which includes the reference point $D_0$ is detected by the irradiation detection unit. In this step $S_2$, the position on the microchip 2 in which the fluorescence is detected is illustrated by a reference numeral D in FIG. 5. In the drawings, a case where 24 detected positions D including the reference point $D_0$ are set, and the fluorescence is detected from the detected positions D in which the number of arrangements $M_1$ of the X-axial direction is arranged in 8 rows, and the number of arrangements $N_1$ of the Z-axial direction is arranged in 3 rows is illustrated as an example.

In a region in which the detected positions D are set, the sample flow passage 22 is included, and the number of detected positions D and an arrangement aspect are not particularly limited but arbitrarily set insofar as the sample flow passage 22 is included in the region. It is preferable that the detected positions D be arranged in a reticular pattern in the X-axial direction and the Z-axial direction, as illustrated. In this case, arrangement intervals W and H of the X-axial direction and the Z-axial direction of the detected positions D are able to be properly set according to a flow passage width (a flow passage diameter) of the sample flow passage 22 and the number of arrangements $M_1$ and $N_1$ of the detected positions D in the X-axial direction and the Z-axial direction. The flow passage width of the sample flow passage 22 is approximately 70 to 100 µm, and when $M_1$ is 8 and $N_1$ is 3, the arrangement intervals W and H are set, for example, to 25 and 75 µm, respectively.

The detection of the fluorescence is performed with respect to one detected position D for a predetermined time. The fluorescence detected for the predetermined time is integrated, converted to the electric signal, and output to the control unit 10. The fluorescence is able to be detected by performing scanning of the laser $L_1$ in the X-axial direction and the Z-axial direction, by sequentially applying the laser to each detected position D, and by detecting the fluorescence to be generated. Alternatively, the fluorescence from each of the detected positions D may be collectively detected by an area imaging element according to the irradiation of the laser $L_1$.

(3) Area Average Value Maximum Position Determination Step $S_3$

In this step $S_3$, the control unit 10 calculates an area average of the integrated value of the detected intensity with respect to each of the detected positions D, and automatically determines the detected position D where the area average becomes higher, preferably, the detected position D where the area average is the maximum value.

The "area average" indicates an average of the integrated value of the detected intensity obtained by one detected position D, and a plurality of detected positions D within a predetermined distance range from the one detected position. In FIG. 5, a case where the area average is an average of the integrated value of the detected intensity obtained by one detected position $D_1$, and detected positions $D_2$ to $D_9$ within the distance range of 2W in the X-axial direction from the detected position $D_1$ and 2H in the Z-axial direction from the detected position $D_1$ is illustrated.

Setting how far the distance range is from the one detected position D as the area average is able to be properly determined according to the flow passage width (the flow passage diameter) of the sample flow passage 22, and the arrangement intervals W and H.

The control unit 10 compares the calculated area average to each of the detected positions D, and determines the detected position D where the area average becomes higher, preferably, the detected position D where the area average is the maximum value. Here, a case where the area average is the maximum value in the detected position $D_1$ will be described.

Since the fluorescence is strongly generated in the sample flow passage 22 through which the calibration bead or the cell flows, it is possible to consider that the sample flow passage 22 is positioned within a region $R_1$ where the detected positions $D_1$ to $D_9$ in which the area average is the maximum value are formed in conjunction.

(4) Area Average Maximum Position Movement Step $S_4$

Figure 6:
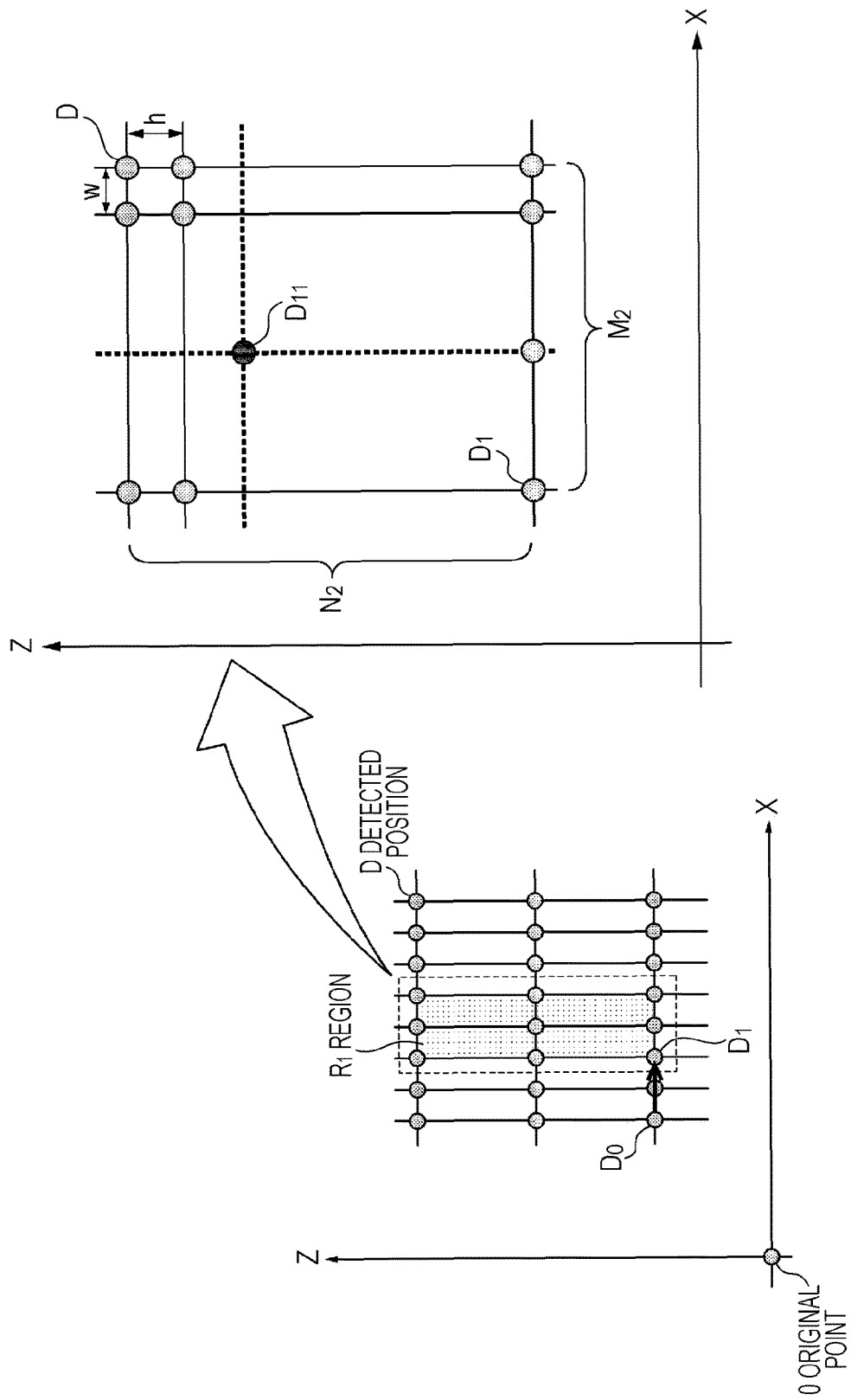
FIG. 6 is a diagram for describing control of an area average maximum position movement step $S_4$ to an integrated value maximum position determination step $S_6$ according to the first embodiment.

When the detected position $D_1$ where the area average is the maximum value is specified, the control unit 10 outputs the movement signal to the position adjustment unit 9, and the position adjustment unit 9 moves the position of the microchip 2 to the detected position $D_1$ from the reference point $D_0$ (refer to an arrow of FIG. 6).

(5) Signal Acquisition Step $S_5$

In this step $S_5$, the detection of the fluorescence which is generated from a plurality of positions within the region $R_1$ where the area average is the maximum value is performed by the irradiation detection unit. The detected positions D of the fluorescence in this step $S_5$ are illustrated in an enlarged view of FIG. 6. In the drawings, a case where the fluorescence is detected from the detected positions D of ($M_2 \times N_2$) in which $M_2$ rows in the X-axial direction and $N_2$ rows in the Z-axial direction are arranged, including the detected position $D_1$ where the area average is the maximum value is illustrated as an example.

Arrangement intervals w and h of the detected positions D in the X-axial direction and the Z-axial direction are able to be properly set according to the flow passage width (the flow passage diameter) of the sample flow passage 22 and the number of arrangements $M_2$ and $N_2$ in the X-axial direction and the Z-axial direction. The number of arrangements $M_2$ and $N_2$ are, for example, 11 and 7, respectively. The row intervals w and h are set, for example, to 5 and 25 μm, respectively. Furthermore, in this step $S_5$, the number of detected positions D and the arrangement aspect are not particularly limited.

The detection of the fluorescence is performed with respect to the one detected position D for the predetermined time. The fluorescence detected for the predetermined time is converted to the electric signal and output to the control unit 10. The fluorescence is detected by performing scanning of the laser $L_1$ in the X-axial direction and the Z-axial direction to sequentially scan each detected position D, and by detecting the fluorescence to be generated. Alternatively, the fluorescence from each of the detected positions D may be collectively detected by the irradiation of the laser $L_1$ according to an area imaging element.

(6) Integrated Value Maximum Position Determination Step $S_6$

In this step $S_6$, the control unit 10 calculates either one or both of the integrated value and the average value of the detected intensity with respect to each of the detected positions D, and a variation coefficient (a CV value) thereof. Hereinafter, a process using the integrated value of the detected intensity and the CV value thereof will be described as an example.

The control unit 10 compares the calculated integrated value of the detected intensity with respect to each of the detected positions D, and determines the detected position D where the integrated value becomes higher, preferably, the detected position D (a first optimal position) where the integrated value is the maximum value. Here, a case where the integrated value is the maximum value in the detected position $D_{11}$ will be described (refer to FIG. 6).

(7) Variation Coefficient Determination Step $S_7$

Figure 7:
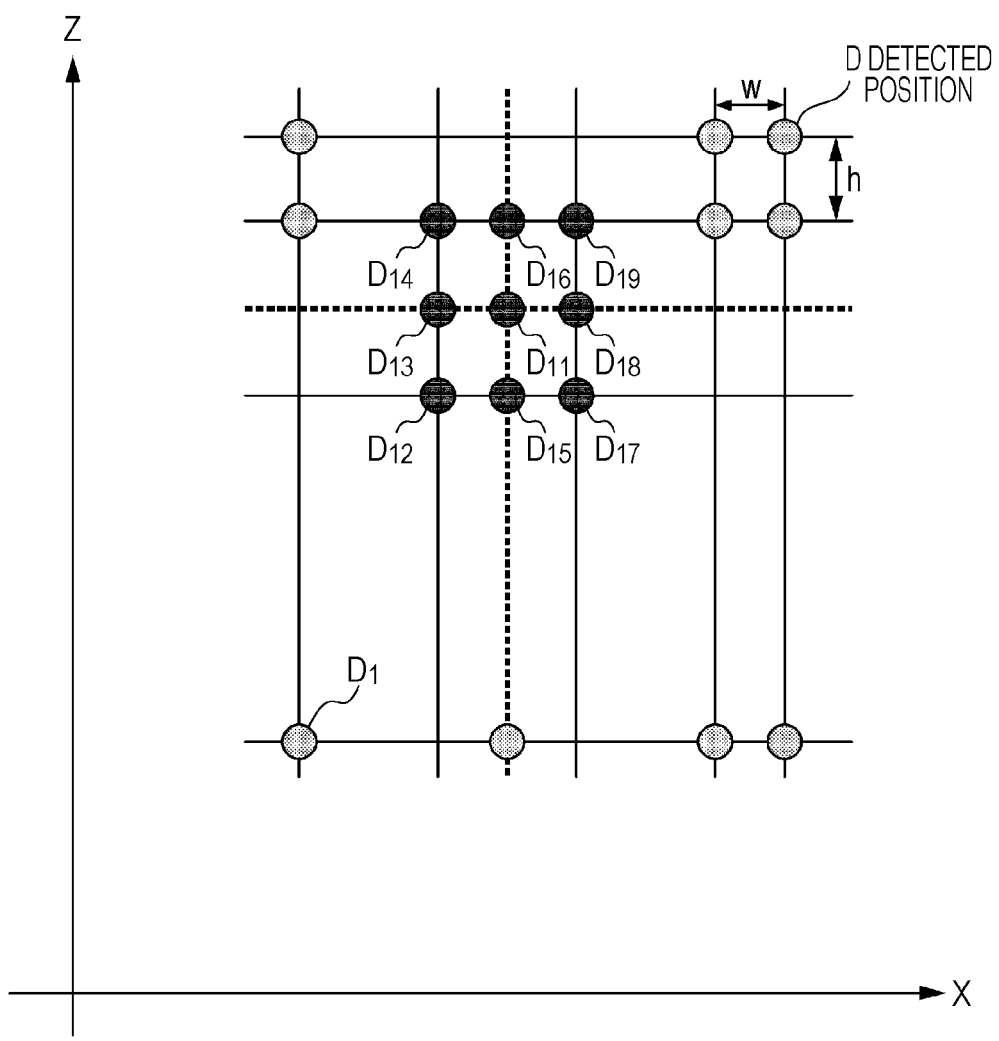
FIG. 7 is a diagram for describing control of a variation coefficient determination step $S_7$ according to the first embodiment.

Next, the control unit 10 compares the CV values between the detected position $D_{11}$ where the integrated value is the maximum value and the adjacent detected positions $D_{12}$ to $D_{19}$, and automatically determines the presence or absence of the detected position D (a second optimal position) to which a CV value smaller than that of the detected position $D_{11}$ is applied (refer to FIG. 7).

(8) Position Optimization Step $S_8$

In step $S_7$, when the detected position D to which the CV value smaller than that of the detected position $D_{11}$ where the integrated value is the maximum value is applied is not found in any of the detected position $D_{11}$ and the adjacent detected positions $D_{12}$ to $D_{19}$, the control unit 10 moves the position of the microchip 2 to the detected position $D_{11}$ from the detected position $D_1$. At this time, both the detected position (the first optimal position) where the integrated value is the maximum value and the detected position (the second optimal position) where the CV value is the minimum value are coincident with each other in the detected position $D_{11}$.

In addition, in step $S_7$, when the detected position D to which the CV value smaller than that of the detected position $D_{11}$ is applied is found in any one of the detected positions $D_{12}$ to $D_{19}$, the control unit 10 moves the position of the microchip 2 to the detected position D (for example, the detected position $D_{18}$) from the detected position $D_1$. At this time, the detected position (the first optimal position) where the integrated value is the maximum value and the detected position (the second optimal position) where the CV value is the minimum value are not coincident with each other.

The detected position $D_{11}$ where the integrated value is the maximum value is a position where the fluorescence is most strongly generated, and is able to be considered as a through-flow position of the calibration bead or the cell in the sample flow passage 22. That is, when the relative position of the microchip 2 with respect to the irradiation detection unit is in the detected position $D_{11}$, the laser $L_1$ emitted from the irradiation detection unit is applied to the through-flow position of the calibration bead or the like in the sample flow passage 22.

In some cases even though the detected position $D_{11}$ where the integrated value is the maximum value is not the through-flow position of the calibration bead or the like in the sample flow passage 22, the integrated value of the fluorescence intensity may be the maximum value. For example, when the detected position $D_{11}$ is coincident with a flow passage wall of the micro-flow passage 22, the fluorescence intensity which is abnormally high due to reflecting, scattering, or the like of the fluorescence may be sporadically detected. In this case, a variation is generated in the fluorescence intensity which is detected in the position, and the CV value of the integrated value of the fluorescence intensity becomes high.

When the detected position $D_{11}$ is coincident with the flow passage wall of the micro-flow passage 22, or the like, it is possible to consider the detected position $D_{18}$ to which a smaller CV value is applied among the detected position $D_{11}$ and the adjacent detected positions as the through-flow position of the calibration bead or the like in the sample flow passage 22. That is, when the relative position of the microchip 2 with respect to the irradiation detection unit is in the detected position $D_{18}$, the laser $L_1$ emitted from the irradiation detection unit is applied to the through-flow position of the calibration bead or the like in the sample flow passage 22.

As described above, in the flow cytometer 1, the relative position of the microchip 2 with respect to the laser $L_1$ is set to the position where the integrated value or the average value of the detected intensity of the fluorescence generated from the microchip 2 by the irradiation of the laser $L_1$ becomes higher or the position where the CV value becomes smaller. Accordingly, in the flow cytometer 1, the through-flow position of the cell in the sample flow passage 22 of the microchip 2, and the optical axis of the laser $L_1$ are automatically positioned with high accuracy, and thus it is possible to simply perform high accuracy measurement.

In addition, in the flow cytometer 1, the optical position of the microchip 2 is optimized by a two-staged procedure of a coarse adjustment for specifying the position where the area average of the integrated value of the detected intensity of the fluorescence becomes higher (steps $S_2$ and $S_3$), and a fine adjustment for specifying the position where the integrated value or the average value becomes higher within the region where the area average becomes higher or the position where the CV value becomes smaller (steps $S_5$ to $S_7$). Accordingly, it is possible to rapidly perform the optimization of the optical position of the microchip 2 with a small processing load.

Figure 8:
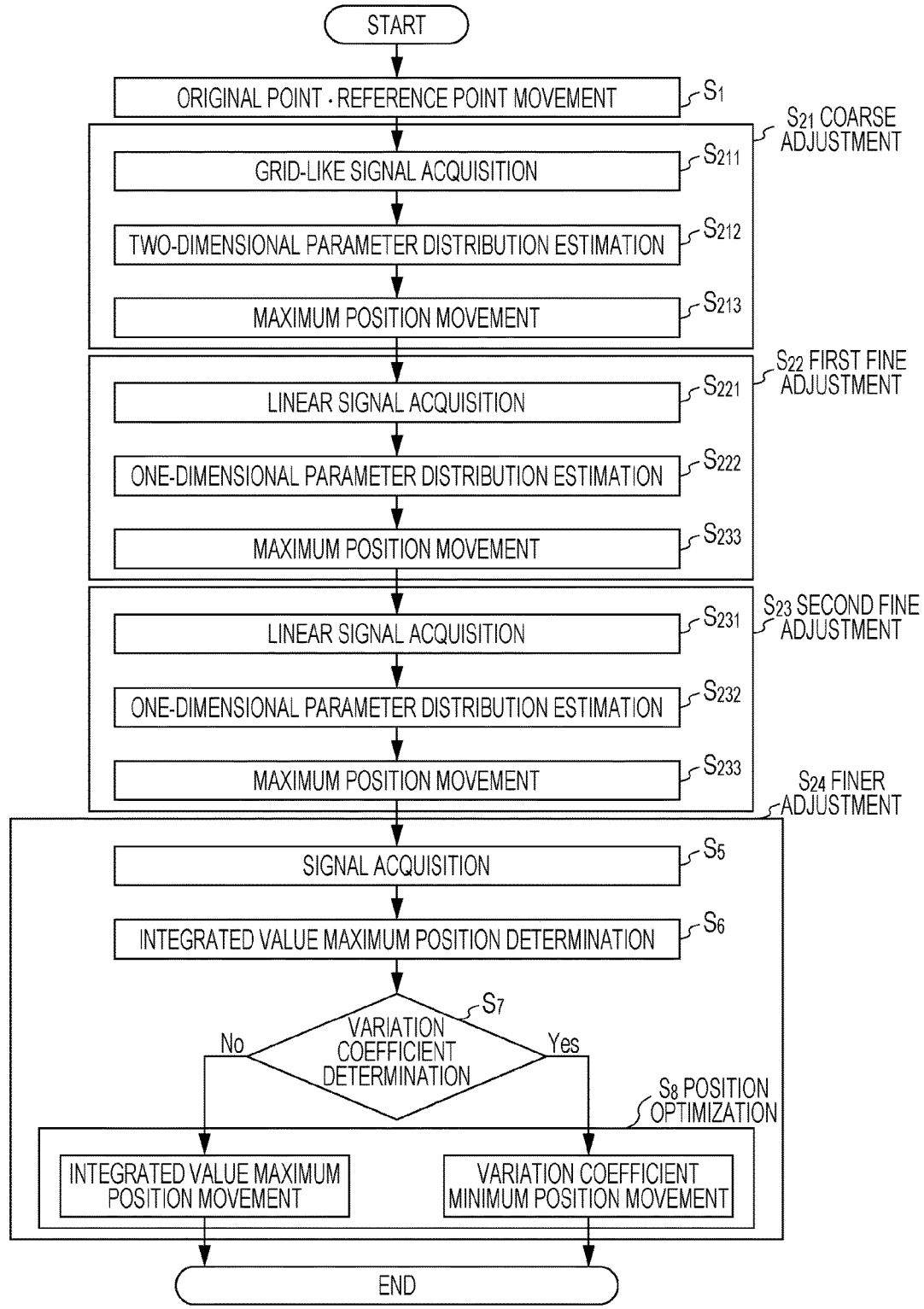
FIG. 8 is a flowchart for describing a control step according to a second embodiment in order to optimize the optical position of the flow cytometer 1.

3. Optimization Control of Optical Position of Microchip-Type Optical Measuring Apparatus According to Second Embodiment of the Present Technology FIG. 8 is a flowchart for describing a control step according to a second embodiment in order to optimize the optical position of the flow cytometer 1. The control step of this embodiment includes a procedure of an "original point•reference point movement step $S_1$", a "coarse adjustment step $S_{21}$", a "first fine adjustment step $S_{22}$", a "second fine adjustment step $S_{23}$", and a "finer adjustment step $S_{24}$". Hereinafter, each procedure will be described. Furthermore, since the original point•reference point movement step $S_1$ is a process which is substantially identical to the original point•reference point movement step $S_1$ of the first embodiment, except that the reference point $D_0$ (refer to FIG. 5 again) corresponds to a reference point $P_0$ illustrated in FIG. 9 (described later), the description thereof will be omitted.

(1) Coarse Adjustment Step $S_{21}$

FIG. 9 is a diagram for describing control of a coarse adjustment step $S_{21}$ according to this embodiment.

The coarse adjustment step $S_{21}$ includes a procedure of a "grid-like signal acquisition step $S_{211}$", a "two-dimensional distribution parameter estimation step $S_{212}$", and a "maximum position movement step $S_{213}$". Hereinafter, each procedure will be described.

(1-1) Grid-Like Signal Acquisition Step $S_{211}$

In this step $S_{211}$, the detection of the fluorescence from a plurality of detected positions $D_{21}$ set in advance is performed by the irradiation detection unit (refer to FIG. 9A). In this step $S_{211}$, a position on the microchip 2 in which the detection of the fluorescence is performed is illustrated by a reference numeral $D_{21}$ in FIG. 9A. In FIG. 9A, a case where the fluorescence is detected from the detected positions $D_{21}$ in which 6 rows in the X-axial direction and 7 rows in the Z-axial direction are arranged, centered on the reference point $P_0$ is illustrated as an example.

In a region in which the detected positions $D_{21}$ are set, the sample flow passage 22 is included, and the number of detected positions $D_{21}$ and the arrangement aspect are not particularly limited but arbitrarily set insofar as the sample flow passage 22 is included in the region. It is preferable that the detected positions $D_{21}$ be arranged in a reticular pattern in the X-axial direction and the Z-axial direction, as illustrated in FIG. 9A. In this case, arrangement intervals $W_2$ and $H_2$ of the detected positions $D_{21}$ in the X-axial direction and the Z-axial direction are able to be properly set according to the flow passage width (the flow passage diameter) of the sample flow passage 22 and the number of arrangements $M_3$ and $N_3$ of the detected positions $D_{21}$ in the X-axial direction and the Z-axial direction. The arrangement intervals $W_2$ and $H_2$ are set, for example, to 62.5 and 125 μm, respectively. The detection of the fluorescence is performed substantially similarly to the signal acquisition step $S_2$ of the first embodiment.

(1-2) Two-Dimensional Distribution Parameter Estimation Step $S_{212}$

In this step $S_{212}$, the control unit 10 assumes that a relationship between each of the detected positions $D_{21}$ and the integrated value or the average value of the detected intensity of the fluorescence follows two-dimensional probability distribution. Further, for the detected position and the detected intensity acquired in step $S_{211}$, and an irradiation profile of the laser indicating a relationship between an irradiation position and an irradiation intensity, the detected intensity of each of the detected positions has a correlative relationship with the irradiation intensity of a corresponding irradiation position. For this reason, it is preferable that the assumed probability distribution be selected according to the irradiation profile of the laser.

For example, when the irradiation profile is in the shape of a top-hat beam as illustrated in FIG. 10A (described later), the control unit 10 is able to assume uniform distribution as a probability distribution model.

On the other hand, when the irradiation profile is in the shape of a Gaussian beam as illustrated in FIG. 10B (described later), normal distribution is able to be assumed as the probability distribution model. Thus, it is possible to adjust the optical position according to the optical characteristic of the laser of the apparatus with high speed and high accuracy by selecting the probability distribution according to the irradiation profile of the laser.

In addition, when it is assumed that the relationship between each of the detected positions $D_{21}$ and the integrated value or the average value of the detected intensity of the fluorescence follows the two-dimensional probability distribution, the control unit 10 estimates a distribution parameter of the probability distribution by a stochastic method, on the basis of stochastic information. For example, the control unit 10 is able to estimate the distribution parameter (an average (a center position of the distribution), dispersion (spread of the distribution), or the like) with respect to each integrated value or average value by a maximum likelihood estimation method.

In this maximum likelihood estimation method, at the time of estimating the relationship between the detected intensity and the detected position to be in the two-dimensional normal distribution, it is possible to estimate where the center position (the position where the detected intensity is maximum) of the two-dimensional normal distribution is at the time of maximizing likelihood, on the basis of the probability distribution model stored in the control unit 10 in advance. According to this maximum likelihood estimation method, it is possible to estimate the position (an optical axis center position of the laser $L_1$) where the detected intensity is maximum with high accuracy even when data of the detected intensity is small.

(1-3) Maximum Position Movement Step $S_{213}$

In this step $S_{213}$, the control unit 10 outputs the movement signal for a position $P_1$ where the integrated value or the average value of the detected intensity in the probability distribution estimated in the probability distribution estimation step $S_{212}$ becomes higher, and preferably, becomes the maximum value to the position adjustment unit 9. Accordingly, as illustrated in FIG. 9C, the position adjustment unit 9 moves the position of the microchip 2 to the position $P_1$ from the reference point $P_0$.

Here, a calculating method of the maximum position will be described with reference to FIG. 10. FIG. 10 is a diagram illustrating a state where the two-dimensional probability distribution is viewed from one direction. In FIG. 10A, top-hat distribution (uniform distribution) is illustrated. When the probability distribution is estimated to be the top-hat distribution, the control unit 10 determines a center position of an edge E1 and an edge E2 in FIG. 10A as the position where the detected intensity is maximum.

On the other hand, in FIG. 10B, Gaussian distribution is illustrated. When the probability distribution is estimated as the Gaussian distribution, as illustrated in FIG. 10B, it is possible to set a position where the integrated value or the average value of the detected intensity has a maximum value b to a position where an inclination is 0 (an inclination a). In the flow cytometer 1, it is preferable that the optical profile of the laser be the Gaussian distribution, and in this case, the distribution of the integrated value or the average value of a plurality of detected intensities may be the Gaussian distribution.

Thus, in the coarse adjustment step $S_{21}$, the integrated value or the average value of the detected intensity of the light in a plurality of detected positions $D_{21}$ is estimated as a specified two-dimensional probability distribution, and it is possible to move the microchip 2 to the position where the integrated value or the average value of the detected intensity of the light in the probability distribution becomes higher, and preferably, becomes the maximum value.

As described above, according to the optical position adjusting method of this embodiment, it is possible to improve position adjustment accuracy of the microchip 2 without increasing the number of detected positions $D_{21}$, by estimating the probability distribution of the detected intensity of each of the detected positions $D_{21}$.

(2) First Fine Adjustment Step $S_{22}$

Figure 11:
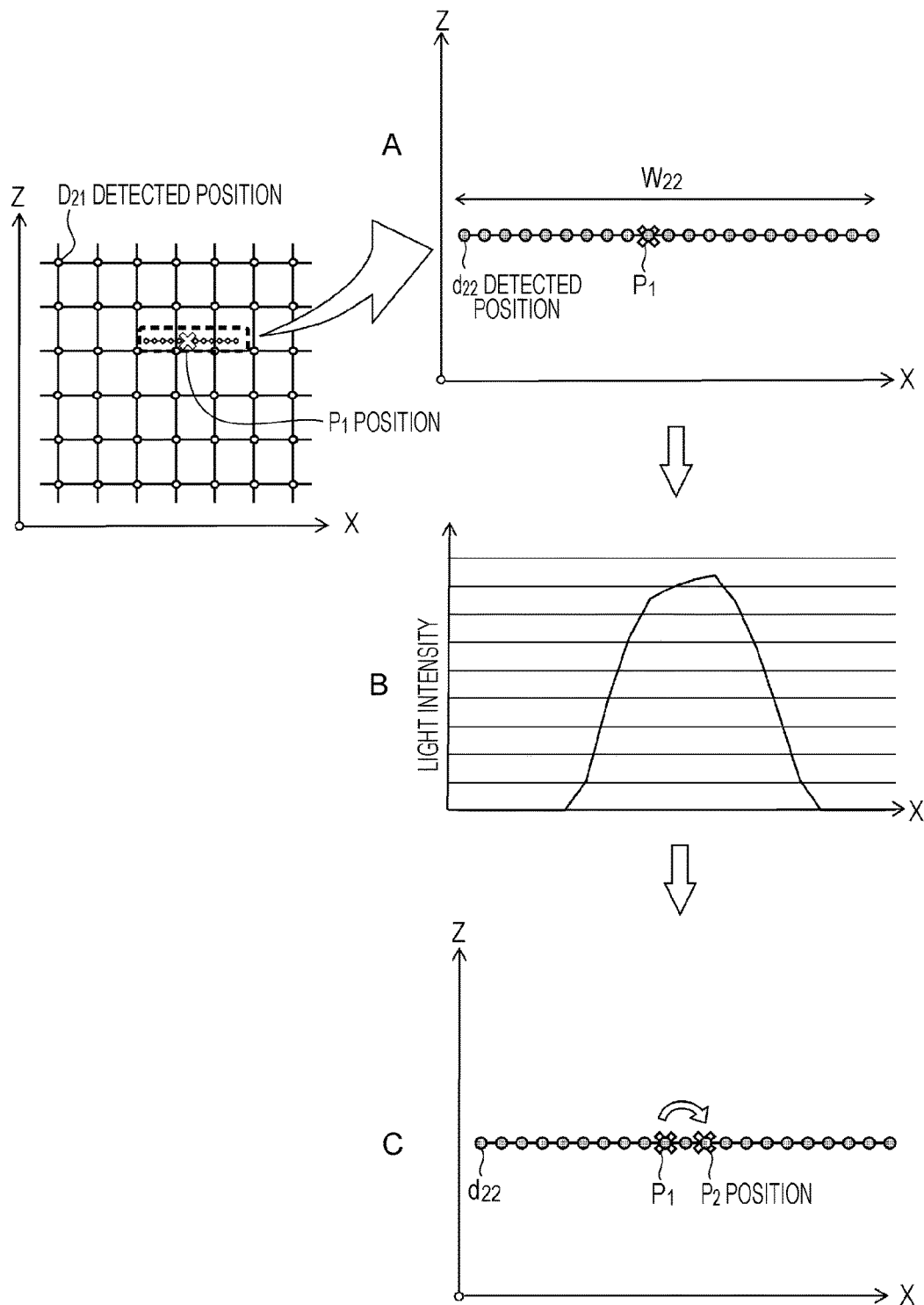
FIG. 11 is a diagram for describing control of a first fine adjustment step $S_{22}$ according to the second embodiment.

FIG. 11 is a diagram for describing control of a first fine adjustment step $S_{22}$ according to this embodiment. The first fine adjustment step $S_{22}$ includes a procedure of a "linear signal acquisition step $S_{221}$", a "one-dimensional distribution parameter estimation step $S_{222}$", and a "maximum position movement step $S_{223}$". Hereinafter, each procedure will be described.

(2-1) Linear Signal Acquisition Step $S_{221}$

In this step $S_{221}$, centered on the position $P_1$ which is set in the coarse adjustment step $S_{21}$, the detection of the fluorescence from a plurality of detected positions $d_{22}$ which are arranged in the X-axial direction is performed (FIG. 11A). An interval $W_{22}$ to be detected and the number of arrangements of the detected positions $d_{22}$ are able to be properly set. In FIG. 11A, a case where 19 detected positions $d_{22}$ are arranged in the X-axial direction, centered on the position $P_1$ is illustrated as an example. The detection of the fluorescence is performed substantially similarly to the signal acquisition step $S_2$ of the first embodiment.

(2-2) One-Dimensional Distribution Parameter Estimation Step $S_{222}$

In this step $S_{222}$, the control unit 10 assumes that a relationship between each of the detected positions $d_{22}$ and the integrated value or the average value of the detected intensity of the fluorescence follows a one-dimensional distribution stored in a memory or the like. For example, when the data of the detected intensity illustrated in FIG. 11B is obtained, the control unit 10 sets the one-dimensional distribution to an Nth-order polynomial model, and thus it is possible to calculate a maximum value on the basis of a least-square method. Setting the one-dimensional distribution to the Nth-order polynomial model allows a variation of the distribution of the optical profile due to a design variation or the like of each component configuring the flow cytometer 1 to be handled with high accuracy, compared to a case where the one-dimensional distribution is set to the normal distribution.

Here, at the time of setting the distribution to the Nth-order polynomial model, while accuracy increases as the order becomes higher, it is susceptible to an effect due to an error of the detected intensity of each of the detected positions $d_{22}$ when the order is too high, and thus it is preferable that the order be, for example, fourth-order.

(2-3) Maximum Position Movement Step $S_{223}$

In this step $S_{223}$, the control unit 10 outputs the movement signal for the position $P_2$ where the integrated value or the average value of the detected intensity in the one-dimensional distribution assumed in the one-dimensional parameter estimation step $S_{222}$ becomes higher, and preferably, becomes the maximum value to the position adjustment unit 9. Accordingly, as illustrated in FIG. 11C, the position adjustment unit 9 moves the position of the microchip 2 to the position $P_2$ from the position $P_1$. Furthermore, a case where the position $P_2$ illustrated in FIG. 11C is on the detected position $d_{22}$ is illustrated as an example, but the position $P_2$ may be between two detected positions $d_{22}$.

Thus, in the first fine adjustment step $S_{22}$, it is possible to adjust the position of the microchip 2 adjusted in the coarse adjustment step $S_{21}$ with high accuracy. Particularly, the position adjustment of the microchip 2 is performed on the basis of the detected intensity of the detected positions $d_{22}$ which are arranged in one direction. For this reason, it is possible to reduce the number of data items to be detected, compared to a case where the position adjustment is performed on the basis of the intensity of the detected positions which are arranged in a plurality of directions, for example, in a reticular pattern. Accordingly, even though the number of arrangements increases, and accuracy of the data increases, it is possible to inhibit data detection time from being increased by narrowing the interval of the detected positions $d_{22}$, compared to a case where the data is two-dimensionally acquired.

(3) Second Fine Adjustment Step $S_{23}$

FIG. 12 is a diagram for describing control of a second fine adjustment step $S_{23}$ according to this embodiment. The second fine adjustment step $S_{23}$ includes a procedure of a "linear signal acquisition step $S_{231}$", a "one-dimensional parameter estimation step $S_{232}$", and a "maximum position movement step $S_{233}$".

As illustrated in FIGS. 12A to 12C, the control of this step $S_{23}$ is substantially identical to the control of the first fine adjustment step $S_{22}$ which is described with reference to FIGS. 11A to 11C, except that the microchip 2 is moved to the position $P_3$ from the position $P_2$ in the Y-axial direction on the basis of the detected intensity of detected positions $d_{23}$ which are arranged in the Y-axial direction, centered on the position $P_2$, instead of moving the microchip 2 to the position $P_2$ from the position $P_1$ in the X-axial direction on the basis of the detected intensity of the detected positions $d_{22}$ which are arranged in the X-axial direction. For this reason, the description thereof will be omitted here.

Here, in the first fine adjustment step $S_{22}$, the position adjustment is performed in the X-axial direction (a flow width direction of the microchip 2), and in the second fine adjustment step $S_{23}$, the position adjustment is performed in the Z-axial direction (a focus direction of the laser $L_1$). Since the Z-axial direction has a wider optical profile width (the detected intensity of the fluorescence is high in a wide range) compared to the X-axial direction, the position adjustment in the Z-axial direction is likely to be performed with high accuracy according to a process performed in the coarse adjustment step $S_{21}$ described above, compared to the position adjustment in X-axial direction. For this reason, in the coarse adjustment step $S_{21}$, it is preferable that the Z-axial direction in which the position adjustment is performed with higher accuracy be fixed first, and then the position adjustment of the microchip 2 in the X-axial direction be performed. Accordingly, it is preferable that the first fine adjustment step $S_{21}$ and the second fine adjustment step $S_{22}$ be performed in this order.

In the second fine adjustment step $S_{23}$, the position adjustment of the microchip 2 is performed in a direction different from the direction of the fine adjustment in the first fine adjustment $S_{22}$, thereby allowing the position adjustment to be performed with higher accuracy.

(4) Finer Adjustment Step $S_{24}$

Figure 13:
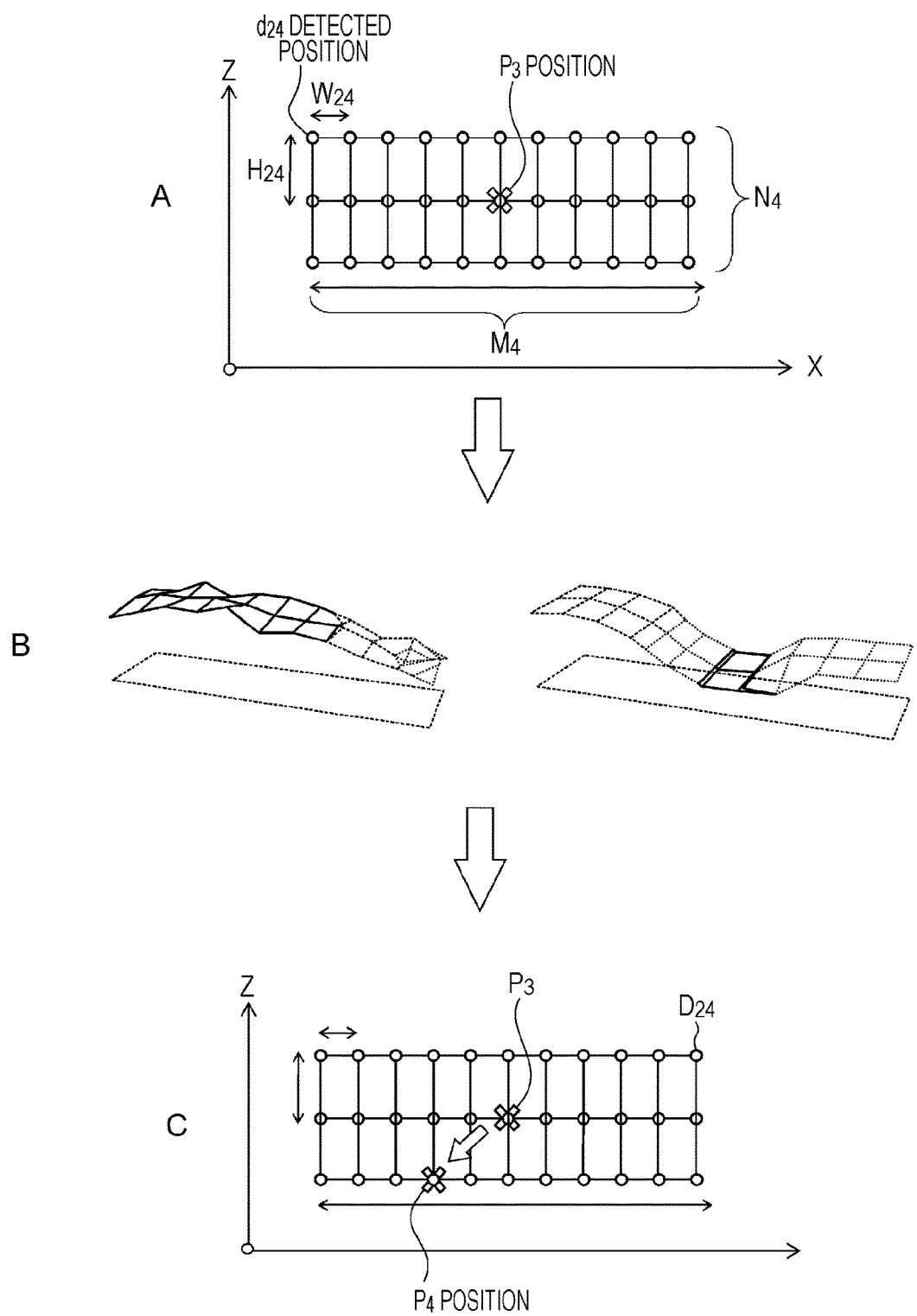
FIG. 13 is a diagram for describing control of a finer adjustment step $S_{24}$ according to the second embodiment.

FIG. 13 is a diagram for describing control of the second fine adjustment step $S_{23}$ according to this embodiment. The finer adjustment step $S_{24}$ includes a procedure of a "signal acquisition step $S_{241}$", an "integrated value maximum position determination step $S_6$", a "variation coefficient determination step $S_7$", and a "position optimization step $S_8$".

As illustrated in FIG. 13A, first, in the signal acquisition step $S_{241}$, the detection of the fluorescence is performed in a plurality of detected positions $d_{24}$, centered on the position $P_3$ which is set in the second fine adjustment step $S_{23}$. In FIG. 13A, a case where the number of arrangements $M_4$ of the X-axial direction is 11 rows, and the number of arrangements $N_1$ of the Z-axial direction is 3 rows is illustrated as an example. The detection of the fluorescence is performed substantially similarly to the signal acquisition step $S_2$ of the first embodiment.

Next, after performing the detection of the fluorescence in the signal acquisition step $S_{241}$, the integrated value maximum position determination step $S_6$, the variation coefficient determination step $S_7$, and the position optimization step $S_8$ are performed substantially similarly to the integrated value maximum position determination step $S_6$, the variation coefficient determination step $S_7$, and the position optimization step $S_8$ of the control step of the first embodiment (refer to FIG. 13B and FIG. 13C).

Thus, the microchip 2 is moved to the most suitable position (moved to $P_4$ from $P_3$ in FIG. 13C).

Furthermore, in this embodiment, each process is described in an order of the "coarse adjustment step $S_{21}$", the "first fine adjustment step $S_{22}$", the "second fine adjustment step $S_{23}$", and the "finer adjustment step $S_{24}$", but, for example, the "coarse adjustment step $S_{21}$", the "first fine adjustment step $S_{22}$", and the "second fine adjustment step $S_{23}$" may be repeated for a plurality of times. In addition, only the "coarse adjustment step $S_{21}$", the "first fine adjustment step $S_{22}$", and the "second fine adjustment step $S_{23}$" are performed at once or a plurality of times, and the "finer adjustment step $S_{24}$" may be omitted.

As described above, according to the optical position adjusting method of this embodiment, the relationship between each of the detected positions and the detected intensity is assumed to follow the specified probability distribution model, and the distribution parameter is estimated on the basis of the stochastic method, thereby allowing the position adjustment of the microchip 2 to be performed with high accuracy in a rapid process, without increasing the number of detected positions.

In the microchip-type optical measuring apparatus according to the present technology, an apparatus for optically measuring an object to be measured which is introduced to a region having the microchip formed therein is broadly included in addition to the microparticle measuring apparatus (the flow cytometer). In addition, the optical position adjusting method according to the present invention is able to be broadly applied to the entire apparatus for optically measuring an object to be measured which is introduced to a region having the microchip formed therein other than the microparticle measuring apparatus (the flow cytometer).

The microchip-type optical measuring apparatus according to the present technology is able to be configured as the following.

(1) A microchip-type optical measuring apparatus, including:

an irradiation detection unit which detects light generated by irradiating a microchip with laser;

a position adjustment unit which changes a relative position of the microchip with respect to the irradiation detection unit; and a control unit which outputs a movement signal for a position in which an integrated value or an average value of a detected intensity of the light in a preset region becomes high to the position adjustment unit.

(2) The microchip-type optical measuring apparatus according to (1), in which the control unit assumes that a relationship between a detected position of the light and the integrated value or the average value of the detected intensity of the light follows a pre-stored probability distribution, estimates a distribution parameter of the probability distribution on the basis of a pre-stored stochastic method, and thus creates the movement signal for the position in which the integrated value or the average value of the detected intensity of the light becomes maximum by the estimation.

(3) The microchip-type optical measuring apparatus according to (2), in which the control unit assumes the probability distribution according to an irradiation profile of the laser.

(4) The microchip-type optical measuring apparatus according to any one of (1) to (3), in which the control unit outputs the movement signal for a position in which a variation coefficient of the integrated value or the average value of the detected intensity of the light in a plurality of preset points becomes minimum to the position adjustment unit.

(5) The microchip-type optical measuring apparatus according to (4), in which the control unit outputs the movement signal for an area in which an area average of the integrated value of the detected intensity in a plurality of preset areas becomes maximum to the position adjustment unit.

(6) The microchip-type optical measuring apparatus according to (5), in which the control unit outputs the movement signal for a position in which the integrated value of the detected intensity in the plurality of preset points becomes maximum to the position adjustment unit.

(7) The microchip-type optical measuring apparatus according to (6), in which the control unit outputs the movement signal for a first optimal position in which the integrated value of the detected intensity in the area of a maximum area average becomes maximum, or for a second optimal position in which the variation coefficient in the area of the maximum area average becomes minimum to the position adjustment unit.

(8) The microchip-type optical measuring apparatus according to (7), in which the control unit outputs the movement signal for the second optimal position to the position adjustment unit when the first optimal position and the second optimal position are different from each other.

(9) The microchip-type optical measuring apparatus according to (1) to (8), in which the microchip-type optical measuring apparatus is a microchip-type microparticle measuring apparatus.

In addition, the optical position adjusting method of a microchip-type optical measuring apparatus according to the present technology is able to be configured as the following.

(1) An optical position adjusting method, including:
a procedure for detecting light which is generated from a microchip by laser irradiation, from a plurality of positions on the microchip; and
a procedure for specifying a position in which an integrated value or an average value of a detected intensity of the light in a region where a plurality of preset points exists becomes maximum.

(2) The optical position adjusting method according to (1), in which in the procedure for specifying the position, a relationship between a detected position of the light and the integrated value or the average value of the detected intensity of the light is assumed to follow a pre-stored probability distribution, a distribution parameter of the probability distribution is estimated on the basis of a pre-stored stochastic method, and thus the position in which the integrated value or the average value of the detected intensity of the light becomes maximum is specified by the estimation.

(3) The optical position adjusting method according to (2), in which in the procedure for specifying the position, the probability distribution is set to two-dimensional distribution.

(4) The optical position adjusting method according to (3), further including a procedure for assuming that a relationship of the integrated value or the average value of the detected intensity of the light from the position in which the integrated value or the average value of the detected intensity of the light is estimated to be maximum by the probability distribution to a predetermined position follows a one-dimensional distribution, and thus for specifying a position in which the integrated value or the average value of the detected intensity of the light becomes maximum by the one-dimensional distribution.

(5) The optical position adjusting method according to any one of (1) to (4), in which in the procedure for specifying the position, the position is set to a position in which a variation coefficient of the integrated value or the average value of the detected intensity of the light in a plurality of preset points becomes minimum.

(6) The optical position adjusting method according to (5), further including a procedure for specifying a position in which an area average of the integrated value of the detected intensity of the light in a plurality of preset areas becomes maximum.

(7) The optical position adjusting method according to (6), further including a procedure for specifying a first optimal position in which the integrated value of the detected intensity in the area of a maximum area average becomes maximum.

(8) The optical position adjusting method according to (7), in which the procedure for specifying the position in which the variation coefficient becomes minimum is a procedure for specifying a second optimal position in which the variation coefficient in the area of the maximum area average becomes minimum.

(9) The optical position adjusting method according to (8), further including a procedure for setting a relative position of the microchip with respect to the laser to the first optimal position or the second optimal position.

(10) The optical position adjusting method according to (9), in which the relative position is set to the second optimal position when the first optimal position and the second optimal position are different from each other.

(11) An optical position adjusting method of a microchip-type optical measuring apparatus, including:
a procedure for detecting light which is generated from a microchip by laser irradiation, from a plurality of positions on the microchip;
a procedure for specifying a position in which an area average of an integrated value of a detected intensity of the light becomes higher;
a procedure for specifying a first optimal position in which the integrated value or an average value of the detected intensity in an area where the area average becomes higher, becomes higher;
a procedure for specifying a second optimal position in which a variation coefficient of the integrated value or the average value of the detected intensity in the area where the area average becomes higher, becomes smaller; and
a procedure for setting a relative position of the microchip with respect to the laser to the first optimal position or the second optimal position.

REFERENCE SIGNS LIST 1 microchip-type optical measuring apparatus
2 microchip
21 orifice
22 sample flow passage
23 sample inlet
3 oscillating element
41 charging unit
42 electrode
51, 52 deflection plate
61 light source
62 detector
81, 82, 83 collection container
9 position adjustment unit
10 control unit
D detected position
$F_1$ fluorescence
$L_1$ laser

The invention claimed is:

1. A microchip-type optical measuring apparatus, comprising:
an irradiation detector configured to detect light generated by irradiating a microchip with a laser;
a position adjustment unit comprising at least one motor, wherein the position adjustment unit is configured to change a relative position of the microchip with respect to the irradiation detector; and
a processor configured to output a movement signal for a position selected based on an integrated value or an average value of a detected intensity of the light in at least one region, wherein:
the processor is configured to use a stochastic method to estimate a distribution parameter of a probability distribution for modeling a relationship between the detected position of the light and the integrated value or the average value of the detected intensity of the light in the at least one region.

2. The microchip-type optical measuring apparatus according to claim 1, wherein the processor is configured to:
generate the movement signal for the selected position based on a result of using the stochastic method to estimate the distribution parameter.

3. The microchip-type optical measuring apparatus according to claim 2, wherein the processor is configured to select the probability distribution according to an irradiation profile of the laser.

4. The microchip-type optical measuring apparatus according to claim 1, wherein the processor is configured to output the movement signal for the selected position based on a variation coefficient of the integrated value or the average value of the detected intensity of the light at a plurality of points.

5. The microchip-type optical measuring apparatus according to claim 4, wherein the processor is configured to output a movement signal for an area based on an area average of the integrated value of the detected intensity in a plurality of areas.

6. The microchip-type optical measuring apparatus according to claim 5, wherein the processor is configured to output the movement signal for the selected position based on the integrated value of the detected intensity at the plurality of points.

7. The microchip-type optical measuring apparatus according to claim 6, wherein the processor is configured to output a movement signal for a first position based on the integrated value of the detected intensity in the area, or for a second position based on the variation coefficient in the area.

8. The microchip-type optical measuring apparatus according to claim 7, wherein the processor is configured to output the movement signal for the second position to the position adjustment unit when the first position and the second position are different from each other.

9. The microchip-type optical measuring apparatus according to claim 8, wherein the microchip-type optical measuring apparatus is a microchip-type microparticle measuring apparatus.

10. An optical position adjusting method of a microchip-type optical measuring apparatus, comprising acts of:
detecting light which is generated from a microchip by laser irradiation, from a plurality of positions on the microchip; and
specifying a position based on an integrated value or an average value of a detected intensity of the light in at least one region, wherein:
the position is specified based on a probability distribution for modeling a relationship between a detected position of the light and the integrated value or the average value of the detected intensity of the light; and
a distribution parameter of the probability distribution is estimated based on a stochastic method.

11. The optical position adjusting method according to claim 10, wherein:
the position is specified based on a result of estimating the distribution parameter.

12. The optical position adjusting method according to claim 11, wherein the probability distribution comprises a two-dimensional distribution.

13. The optical position adjusting method according to claim 12, further comprising acts of:
estimating the distribution parameter of the probability distribution based on the stochastic method; and
specifying the position based on the integrated value or the average value of the detected intensity of the light.

14. The optical position adjusting method according to claim 10,
wherein the position is set to a position based on a variation coefficient of the integrated value or the average value of the detected intensity of the light at a plurality of points.

15. The optical position adjusting method according to claim 14, wherein:
the position is specified further based on an area average of the integrated value of the detected intensity of the light in a plurality of areas.

16. The optical position adjusting method according to claim 15, further comprising an act of:
specifying a first position based on the integrated value of the detected intensity in a selected area.

17. The optical position adjusting method according to claim 16,
wherein the position is specified based on a second position specified based on the variation coefficient in the area.

18. The optical position adjusting method according to claim 17, further comprising an act of:
setting a relative position of the microchip with respect to the laser to the first position or the second position.

19. The optical position adjusting method according to claim 18, wherein the relative position is set to the second position when the first position and the second position are different from each other.

20. An optical position adjusting method of a microchip-type optical measuring apparatus, comprising acts of:
detecting light which is generated from a microchip by laser irradiation, from a plurality of positions in an area on the microchip;
specifying a position based on an area average of an integrated value of a detected intensity of the light;
specifying a first position based on the integrated value or an average value of the detected intensity in the area, wherein:
the first position is specified based on a probability distribution for modeling a relationship between a detected position of the light and the integrated value or the average value of the detected intensity in the area; and
a distribution parameter of the probability distribution is estimated based on a stochastic method;

specifying a second position based on a variation coefficient of the integrated value or the average value of the detected intensity in the area; and setting a relative position of the microchip with respect to the laser to the first position or the second position.

* * * * *